(12) United States Patent
Bacino et al.

(10) Patent No.: US 9,808,605 B2
(45) Date of Patent: Nov. 7, 2017

(54) CONTROLLED POROSITY DEVICES FOR TISSUE TREATMENTS, METHODS OF USE, AND METHODS OF MANUFACTURE

(71) Applicant: W. L. Gore & Associates, Inc., Newark, DE (US)

(72) Inventors: John E. Bacino, Landenberg, PA (US); Carey V. Campbell, Flagstaff, AZ (US); Edward H. Cully, Flagstaff, AZ (US); Benjamin M. Trapp, Flagstaff, AZ (US); Michael J. Vonesh, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 470 days.

(21) Appl. No.: 13/644,251

(22) Filed: Oct. 3, 2012

(65) Prior Publication Data
US 2013/0226131 A1    Aug. 29, 2013

Related U.S. Application Data

(60) Provisional application No. 61/544,170, filed on Oct. 6, 2011, provisional application No. 61/697,262, filed on Sep. 5, 2012.

(51) Int. Cl.
*A61M 25/10* (2013.01)
*A61L 29/14* (2006.01)
(Continued)

(52) U.S. Cl.
CPC ........... *A61M 25/10* (2013.01); *A61L 29/041* (2013.01); *A61L 29/146* (2013.01);
(Continued)

(58) Field of Classification Search
CPC .......... A61M 25/10; A61M 2025/1075; A61M 2025/1013; A61M 2025/1015;
(Continued)

(56) References Cited

U.S. PATENT DOCUMENTS 4,417,576 A * 11/1983 Baran ....................... 128/207.15
5,049,132 A    9/1991 Shaffer et al.
(Continued)

FOREIGN PATENT DOCUMENTS

JP    1996-098893    4/1996
WO    97/10871       3/1997
(Continued)

OTHER PUBLICATIONS

International Search Report and Written Opinion for PCT/US2012/058599 mailed Feb. 5, 2013, corresponding to U.S. Appl. No. 13/644,251.

*Primary Examiner* — Imani Hayman
*Assistant Examiner* — Nilay Shah
(74) *Attorney, Agent, or Firm* — Kilpatrick Townsend & Stockton, LLP

(57) ABSTRACT

In various embodiments, a device is provided comprising a balloon configured to expand to an expanded state in response to introduction of a fluid at a first pressure, wherein the fluid perfuses through the balloon above a second pressure, the second pressure being the same or greater than the first pressure. In various embodiments, a method comprising fabricating a balloon configured to expand to an expanded state in response to introduction of a fluid at a first pressure, wherein the fluid perfuses through the balloon above a second pressure, the second pressure being at or greater than the first pressure, disposing the balloon on an elongate member having a lumen, placing the lumen in fluid communication with an interior volume of the balloon.

14 Claims, 15 Drawing Sheets

(51) Int. Cl.
*A61L 29/04* (2006.01)
*A61F 2/958* (2013.01)

(52) U.S. Cl.
CPC ........... *A61M 25/104* (2013.01); *A61F 2/958* (2013.01); *A61F 2002/9583* (2013.01); *A61M 25/1029* (2013.01); *A61M 2025/105* (2013.01); *A61M 2025/1075* (2013.01); *F04C 2270/0421* (2013.01)

(58) Field of Classification Search
CPC ........... A61M 25/1027; A61M 25/1029; A61F 2/958; A61F 2002/9583
USPC ......... 604/500, 103, 103.01, 103.02, 103.03, 604/103.06, 103.08, 103.11, 101.01, 604/101.02
See application file for complete search history.

(56) References Cited

U.S. PATENT DOCUMENTS

| | | | |
|---|---|---|---|
| 5,087,244 A | | 2/1992 | Wolinsky et al. |
| 5,213,576 A | | 5/1993 | Abiuso et al. |
| 5,234,457 A | * | 8/1993 | Andersen ...................... 606/198 |
| 5,282,785 A | | 2/1994 | Shapland et al. |
| 5,389,314 A | | 2/1995 | Wang |
| 5,458,568 A | | 10/1995 | Racchini et al. |
| 5,569,198 A | | 10/1996 | Racchini |
| 5,752,934 A | * | 5/1998 | Campbell et al. ......... 604/96.01 |
| 5,925,074 A | | 7/1999 | Gingras et al. |
| 6,048,332 A | | 4/2000 | Duffy et al. |
| 6,364,856 B1 | * | 4/2002 | Ding et al. ............... 604/103.02 |
| 6,375,637 B1 | * | 4/2002 | Campbell et al. ............ 604/103 |
| 6,395,208 B1 | | 5/2002 | Herweck et al. |
| 6,544,221 B1 | | 4/2003 | Kokish et al. |
| 6,547,804 B2 | * | 4/2003 | Porter et al. .................. 606/195 |
| 6,623,452 B2 | | 9/2003 | Chien et al. |
| 6,695,830 B2 | | 2/2004 | Vigil et al. |
| 6,733,474 B2 | | 5/2004 | Kusleika |
| 6,939,374 B2 | | 9/2005 | Banik et al. |
| 7,090,655 B2 | | 8/2006 | Barry |
| 7,108,684 B2 | | 9/2006 | Farnan |
| 7,306,729 B2 | * | 12/2007 | Bacino et al. ........... 210/500.22 |
| 7,637,886 B2 | | 12/2009 | Herweck et al. |
| 7,947,015 B2 | | 5/2011 | Herweck et al. |
| 8,034,022 B2 | | 10/2011 | Boatman |
| 8,043,258 B2 | | 10/2011 | Ostroot |
| 8,049,061 B2 | | 11/2011 | Ehrenreich et al. |
| 2003/0060814 A1 | * | 3/2003 | Capuano ................ A61B 18/02 606/21 |
| 2004/0236308 A1 | | 11/2004 | Herweck et al. |
| 2006/0136032 A1 | * | 6/2006 | Legarda et al. ............. 623/1.11 |
| 2006/0211983 A1 | * | 9/2006 | Davidson et al. ......... 604/96.01 |
| 2008/0015500 A1 | | 1/2008 | Herweck et al. |
| 2008/0140002 A1 | | 6/2008 | Ramzipoor et al. |
| 2009/0270787 A1 | | 10/2009 | Oepen et al. |
| 2010/0010470 A1 | * | 1/2010 | Bates .................... A61L 29/126 604/509 |
| 2010/0189876 A1 | | 7/2010 | Kokish et al. |
| 2010/0292641 A1 | | 11/2010 | Wijay et al. |
| 2010/0331947 A1 | * | 12/2010 | Shalev et al. ................ 623/1.11 |
| 2011/0137245 A1 | | 6/2011 | Schaeffer et al. |
| 2011/0160575 A1 | | 6/2011 | Beyar et al. |
| 2012/0064273 A1 | | 3/2012 | Bacino |
| 2012/0071715 A1 | | 3/2012 | Beyar et al. |

FOREIGN PATENT DOCUMENTS

| | | |
|---|---|---|
| WO | 2008/021020 | 2/2008 |
| WO | WO 2008021020 A2 * | 2/2008 |
| WO | 2008/048387 | 4/2008 |
| WO | 2009/070209 | 6/2009 |

* cited by examiner

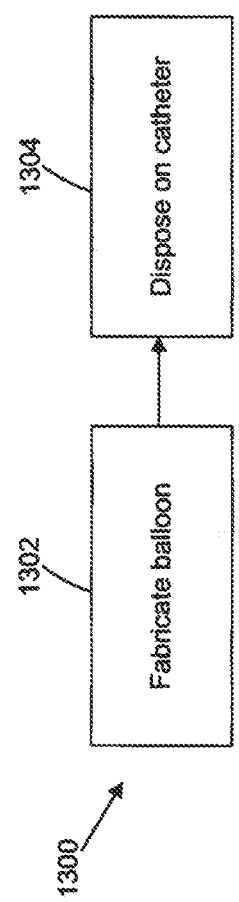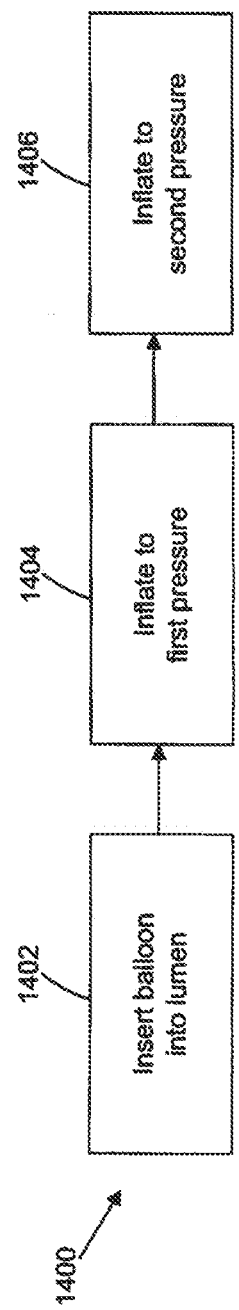

CONTROLLED POROSITY DEVICES FOR TISSUE TREATMENTS, METHODS OF USE, AND METHODS OF MANUFACTURE

CROSS-REFERENCE TO RELATED APPLICATION

This application is a non-provisional of and claims priority to U.S. Provisional No. 61/544,170, filed on Oct. 6, 2011 and entitled "Controlled Porosity Devices for Tissue Treatments, Methods of Use, and Methods of Manufacture" and U.S. Provisional No. 61/697,0262 filed on Sep. 5, 2012 and entitled "Controlled Porosity Devices for Tissue Treatments, Methods of Use, and Methods of Manufacture," wherein such provisional applications are hereby incorporated by reference in their entirety.

FIELD OF THE DISCLOSURE

The present disclosure relates, generally, to perfusion devices, such as balloons, for tissue treatments, methods of use, and methods of manufacture.

BACKGROUND OF THE DISCLOSURE

Balloons intended for use within a mammalian body, such as a human, are employed in a variety of medical procedures, including dilation of narrowed blood vessels, placement of stents and other implants, temporary occlusion of blood vessels, drug delivery, thrombectomy, embolectomy, angioplasty, other endovascular procedures, and other procedures within a lumen of a mammalian body such as a human body. In this regard, as used herein, the term "body" can comprise a mammalian body such as a human body or other animal body.

In a typical application, a balloon (often coupled with a catheter or guidewire) is advanced to the desired location in the vascular system or other lumen of the body. The balloon is then hydraulically expanded in accordance with a medical procedure. Thereafter, the pressure is removed from the balloon, allowing the balloon to contract and permit removal of the catheter and, in many cases, the balloon.

Procedures such as these are generally considered minimally invasive, and are often performed in a manner which minimizes disruption to the patient's body. As a result, balloons are often inserted from a location remote from the region to be treated. For example, during angioplasty procedures involving coronary vessels, the balloon catheter is typically inserted into the femoral artery in the groin region of the patient, and then advanced through vessels into the coronary region of the patient. These catheters typically include some type of radiopaque marker to allow the physician performing the procedure to monitor the progress of the catheter through the body.

Non-compliant balloons employ a balloon made of relatively strong but generally non-porous and inelastic material (e.g., nylon, polyester, etc.) folded into a compact, small diameter cross section. These relatively stiff balloons are used to compact hard deposits in vessels. Due to the need for strength and stiffness, these devices are rated to employ high inflation pressures, usually up to about 8 to about 30 atmospheres depending on balloon diameter and specific need. They tend to be self-limiting as to diameter in that they will normally distend up to the rated (nominal) diameter and not distend appreciably beyond this diameter.

Once a conventional, non-compliant balloon is inflated to its self-limiting diameter, the application of additional pressure can cause rupture of the balloon, creating a hazardous condition. Thus, the pressure within a conventional, non-compliant balloon must be carefully monitored during use.

In addition, conventional, non-compliant balloons are made to be fluid tight (that is, without holes, openings, or pores) in order to achieve and maintain the typically high pressures of the intended application. Therefore, a typical non-compliant balloon will not provide a feature whereby fluid can be transferred from inside the balloon, through the balloon wall, to regions outside the balloon. Thus, for example, conventional, non-compliant balloons are not suitable for the delivery of a therapeutic agent via perfusion. Similarly, other desirable results of perfusion cannot be realized. As can be appreciated, there can be other problems associated with the use of conventional, non-compliant balloons.

Thus, there is a need for systems and methods that address one or more of the problems associated with conventional, non-compliant balloons. For example, there is a need for systems and methods for non-compliant balloons that are not susceptible to failure (e.g., rupture) at a wide pressure range. Likewise, there is a need for systems and methods for non-compliant balloons that can function to become selectively porous and provide localized perfusion and/or therapeutic agent delivery. In addition, there is a need for non-compliant balloons capable of luminal distention or occlusion over a wide pressure range and concomitantly provide for the selective, controlled transfer of fluids from balloon to regions external to the balloon.

SUMMARY OF THE DISCLOSURE

The present disclosure provides devices with selectively controlled porosity for tissue treatments, methods of use, and methods of manufacture. In various embodiments, a device is provided comprising a balloon configured to expand to an expanded state in response to introduction of a fluid at a first pressure, wherein the fluid perfuses through the balloon above a second pressure, the second pressure being at least one of equal to and greater than the first pressure.

In various embodiments, a device comprising an expandable balloon with a wall of selected thickness is configured to expand to a nominal diameter whereupon the inflation fluid (or other fluid contained within the balloon structure) is transferred across the balloon wall due to internal hydraulic pressures exceeding the water entry pressure (WEP) of the balloon wall. In various embodiments, a device is provided comprising a balloon configured to expand in response to introduction of a fluid at a first pressure, and wherein at a second pressure at or above the first pressure, fluid is transferred through the balloon wall. In various embodiments, upon a selected decrease in inflation pressure, balloons of the present disclosure will cease to perfuse yet remain capable of staying at, or being re-inflated to, their nominal or working diameter, for example, capable of dilating the same or another treatment target, optionally followed by fluid transfer through the wall of the balloon.

In various embodiments, balloons of the present disclosure are constructed such that all or only a portion (or portions) of their wall dimension allow the transfer of fluid from internal to external of the balloon.

In various embodiments, an expandable balloon is provided which upon over-inflation, i.e., if the balloon's maximum "working pressure" is exceeded (its terminal pressure is reached), fluid is transferred through at least a portion of the wall of the balloon, avoiding catastrophic failure of the balloon.

In various embodiments, the controlled porosity, expandable balloon of the present disclosure can be configured to be conformable within a body lumen or cavity. In various embodiments, balloons in accordance with the present disclosure can be constructed so as to be length-adjustable, evertable and/or of various shape and dimension. In various embodiments, balloons of the present disclosure can be incorporated on steerable catheters. In various embodiments, the balloons of the present disclosure can be overlaid by covers which provide functionality other than perfusion. For example, the balloons could be overlain with a template having apertures that constrains a portion of the balloon but permits the portions of the balloon proximate the apertures to distend outwardly relative to the template. In various embodiments, the balloons described herein can be configured not as dilation balloons per se, but as catheters, capable of fluid delivery.

In other embodiments, balloons of the present disclosure can be used to deliver a wide range of therapeutic agents. In various embodiments the balloon inflation media comprises said agents. In various embodiments, such agents are supplied in the inflation fluid, i.e., in a premixed form supplied through the proximal hub of the balloon catheter. In one embodiment, such agents are disposed in, for example, a soluble or hydratable form within the balloon structure (e.g., on the balloon catheter or inner surface of the balloon wall) and subsequently dissolved or hydrated by the inflation fluid before being transferred through the balloon wall. Alternatively, the agent can be positioned on the exterior of the balloon or within the layers of the balloon wall and is dissolved or hydrated and/or caused to be released upon fluid transfer through the wall of the balloon. In various embodiments, balloons as described herein can be used to deliver other compounds to the body, including contrast (or other visualization) agents, such as barium or iodine containing agents. In various embodiments, balloons of the present disclosure can be filled with contrast agents and used to locate side branch vessels which would normally be occluded at their ostia by a typical balloon in contact with them. In various embodiments, the balloons can be configured to release a visualization agent at only a portion of the balloon wall surface, the advantage being to limit the amount of visualization agent released into the body.

In various embodiments, balloons of the present disclosure can be used to both dilate a body cavity or lumen and deliver a fluid in the region of said dilation without the use of separate devices. In various embodiments, the balloons are constructed so as to withstand pressures of between about 8 atm and about 30 atm. In various embodiments, the balloon possesses a diameter of above about 4 mm. In various embodiments the dilation so performed is Percutaneous Transluminal Angioplasty (PTA). In one embodiment, the balloons of the present disclosure are used to occlude blood flow in a vessel with only limited or no dilation. In another embodiment, the balloons of the present disclosure are used to occlude blood flow in a vessel with only dilation, followed by delivery, through the wall of the balloon, of a therapeutic agent, for example, a sclerosing agent, for example, for vein ablation. In certain embodiments, materials for the wall of the balloon are selected to be controllably porous to liquids but allow the passage of gases. This allows a clinician to prepare the balloon before use by expelling gases within the balloon.

In various embodiments, a method is provided comprising fabricating a balloon configured to expand to an expanded state in response to introduction of a fluid at a first pressure, wherein the fluid perfuses through the balloon above a second pressure, the second pressure being greater or equal to the first pressure, disposing the balloon on an elongate member having a lumen, placing the lumen in fluid communication with an interior volume of the balloon.

In various embodiments, the balloon optionally comprises a weeping control layer, a reinforcing layer, and a seal layer, wherein at least one of the weeping control layer, the reinforcing layer, and the seal layer are comprised of ePTFE.

In various embodiment, the balloon can comprise a first porous membrane configured to begin perfusing at a pressure, the pressure being equal to or greater than that required to reach nominal diameter, size, or dimension, and a second porous membrane constructed to withstand the hydrostatic load generated by the first membrane upon inflation. The first porous membrane can be configured not to begin perfusion until the pressure is at least 10 atm, or in other embodiments, the first porous membrane will not begin perfusing until at least 25 atm In various embodiments, methods are provided for selecting materials to construct balloon walls capable of inflation to a nominal diameter, followed by perfusion, based upon the porosity (e.g., pore size) of the materials at various hydraulic pressures. In some embodiments, materials are selected based upon their water entry pressure characteristics. In certain embodiments, porosity of materials selected to construct balloons of the present disclosure can be altered by modifying base materials used, e.g., via coating, imbibing, filling, densifying, compounding, coalescing, layering, treating (e.g., with a wetting agent), and the like. In some embodiments, the material(s) selected comprise highly-oriented materials. In some embodiments, the material(s) selected feature a node and fibril microstructure. In another embodiment, the material(s) selected comprise a porous microstructure. In various embodiments, the material(s) selected comprise ePTFE. In some embodiments, the materials selected comprise an ultrahigh molecular weight polyethylene. In some embodiments, the materials comprise electrospun membranes. In various embodiments, the microstructure of the material(s) selected does not substantially change between an inflated state and the states during perfusion.

In various embodiments, the rate and amount of fluid transfer through the walls of balloons of the instant disclosure (and desired pressures to affect same) can be controlled by selection of fluids intended to pass through the balloon walls. For example, the viscosity of such fluids, alone or in combination with porosity of selected construction materials will so affect such performance. As another example, the surface energy of the materials selected and used to construct the balloon walls can be altered (e.g., by a wetting agent) to influence performance. Such an agent can be incorporated in the device at manufacture or applied by a clinician at the time of use.

Further areas of applicability will become apparent from the detailed description provided herein. It should be understood that the description and specific examples are intended for purposes of illustration only and are not intended to limit the scope of the present disclosure.

BRIEF DESCRIPTION OF THE DRAWINGS

The accompanying drawings are included to provide a further understanding of the present disclosure and are incorporated in and constitute a part of this specification, illustrate embodiments of the present disclosure and together with the description serve to explain the principles of the disclosure.

FIG. 13 illustrates an exemplary method of manufacture, in accordance with various embodiments;

FIG. 14 illustrates an exemplary method, in accordance with various embodiments;

DETAILED DESCRIPTION

Figure 1A:
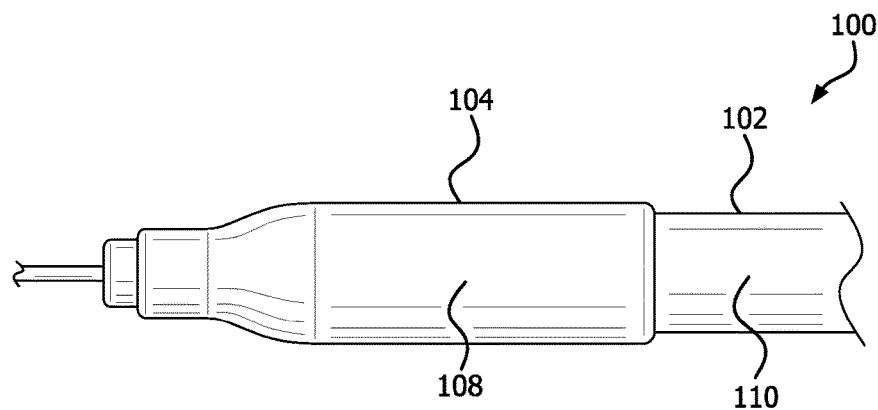
FIGS. 1A and 1B illustrate an uninflated balloon from an exterior perspective and in cross section of same, in accordance with various embodiments.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting. Finally, although the present disclosure can be described in connection with various principles and beliefs, the present disclosure should not be bound by theory.

As used in this application, the term "perfusion" means the passage of a fluid through a membrane (e.g. weeping control layer) and/or filter material. The term "perfusion rate" means the volume of perfusion per unit time and the term "perfusion resistance" means the restriction of perfusion during flow through membranes or media with small pores.

As used in this application, the term "permeability" means the ability to transmit fluids (liquid or gas) through the pores of a membrane or filter material when the material is subjected to a differential pressure across it. Permeability can be characterized by Gurley number, Frazier number, or water flux rate.

As used in this application, the term "pore size" means the size of the pores in porous membranes. Pore size can be characterized by bubble point, mean flow pore size, or water entry pressure, as described in more detail herein.

As used in this application, the term "water entry pressure" means the minimum pressure required to drive water through the largest opening of a membrane, as further described herein. "Threshold perfusion pressure" means the pressure required to obtain detectable (e.g., visibly detectable) perfusion of a fluid on the outer surface of the membrane.

Increased permeability is manifested by lower Gurley numbers (i.e., less time for a given volume of air to pass through the membrane at a given pressure), higher Frazier numbers (i.e., the flow rate of air through the membrane for a given pressure drop and sample area), and higher water flux rates. Pore size is characterized by the bubble point (BP), mean flow pore size, or water entry pressure ("WEP") values. Higher bubble point values (the pressure required to pass a bubble of air through a wetted sample of membrane) and higher WEP values indicate smaller pore sizes.

As used herein, the term "to inflate" means to introduce fluid (e.g., an influx of fluid) into a balloon's interior volume. As used herein, the term "inflated" means a balloon above a minimum pressure, such as at a first pressure or above a first pressure. A fluid can comprise a liquid or gel.

In various embodiments, balloons, for example, balloons, are disclosed that expand to a fixed (i.e., predetermined) diameter in response to the application of internal pressure and perfuse in response to the application of internal pressure. Internal pressure can be defined as the pressure exerted on at least a portion of an interior wall of a balloon. In such a manner, in various embodiments, a balloon can be inflated to a first pressure sufficient for the balloon to reach a fixed diameter. Then, at a desired time, the internal pressure can be increased from the first pressure, causing perfusion of a fluid through the balloon. Stated another way, balloons, in accordance with various embodiments, have a WEP and/or bubble point tailored to be at or above that which is required for inflation to a fixed diameter. For example, in various embodiments, a non-compliant balloon can inflate to a fixed diameter at a pressure below the WEP and/or bubble point and then additional internal pressure can be exerted to reach or exceed the WEP and/or bubble point. Thus, expansion and perfusion are independently controllable, a feature not found in conventional balloons. In further embodiments, a balloon can inflate to a fixed diameter at a pressure equal to or near the WEP and/or bubble point, thus causing weeping.

In various embodiments, the rate of perfusion is proportional to the internal pressure. Thus, internal pressures above the second pressure can result in faster perfusion rates, depending upon a variety of factors, including the materials and configuration of the balloon. As perfusion rates rise, internal pressure generally drops. Accordingly, perfusion can be controlled by the internal pressure applied and the rate of change of the internal pressure applied. It should be noted that in various embodiments, perfusion can occur in response to an initial high pressure that acts to "wet" a balloon. As used herein, the terms "wet", "wetting" and "wetted" refer to the displacement of air in a microporous material by a fluid. In addition, wetting can be facilitated by coating the microporous material with a wetting agent, e.g., polyvinyl alcohol. After wetting, a balloon can require lower pressure than the initial pressure to perfuse at the same rate.

In various embodiments, a balloon, as a result of selecting an appropriate weeping control layer, can produce at least two perfusion pressure threshold events. In addition, the pressure at which the balloon begins to perfuse after a first (or previous) perfusion cycle is within 10% or within about 1 to about 3 atm of the first (or previous) perfusion threshold pressure, provided the balloon is not inflated above about 1 atm, about 3 atm, or about 5 atm of the first (or previous) perfusion threshold pressure. As such, a balloon that has been deflated after a perfusion cycle can be re-inflated and will begin to perfuse at a pressure that is similar to the previous pressure threshold. For example, a balloon that comprises a balanced film membrane as the weeping control layer can be re-inflated and will not begin to perfuse until a pressure is reached that is within 10% of the first (or previous) threshold pressure. In an embodiment, the film of weeping control layer can comprise a balance ration of between 1:1 and 5:1. In an embodiment, the weeping control layer of balloon can comprise a membrane that has substantially stable porous microstructure when the pressure has not gone above about 3 atm of the threshold perfusion pressure. Stated differently, the porous microstructure is only minimally deformed after a perfusion cycle provided the pressure within the balloon does not exceed above about 1 atm to about 5 atm of the perfusion threshold pressure. Thus, the balloon will cease weeping once pressure is reduced, i.e., the balloon is deflated.

In various embodiments, a balloon can have a failsafe internal pressure that comprises a third internal pressure, referred to herein as a max or terminal pressure. In an embodiment, a balloon can perfuse at a rate substantially equal to or greater than the rate at which fluid can be delivered, i.e. rate of fluid entry with the use of a balloon inflation device (such as Endoflator®), thereby resulting in a loss of or cap to the internal pressure. Thus, it can be difficult to raise the interior pressure of a balloon above the maximum pressure because the internal pressure is relieved via a high rate of perfusion. Accordingly, in various embodiments, balloons provided herein are resistant to a failure (e.g., a rupture). As noted above, conventional non-compliant balloons are susceptible to failure via rupturing.

Figure 1B:
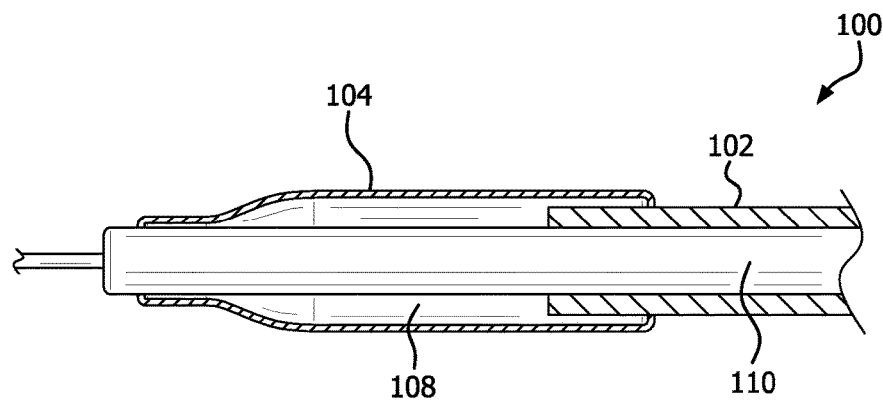

For example, with reference to FIG. 1A, an uninflated balloon assembly 100 is shown having balloon 104 disposed on elongate member 102. Elongate member 102 has a lumen 110 that is in fluid communication with balloon interior 108. In various embodiments, a protector cover can optionally be disposed over balloon 104. FIG. 1B shows the embodiment of FIG. 1A in cross section. As shown, fluid from lumen 110 can enter balloon interior 108. Lumen 110 is connected to various other components, for example a syringe, or inflator/deflator or pump. An apparatus such as a syringe or pump can exert pressure on a fluid (e.g., saline or a gel) in lumen 110 that exerts pressure on the balloon interior 108.

Figure 2A:
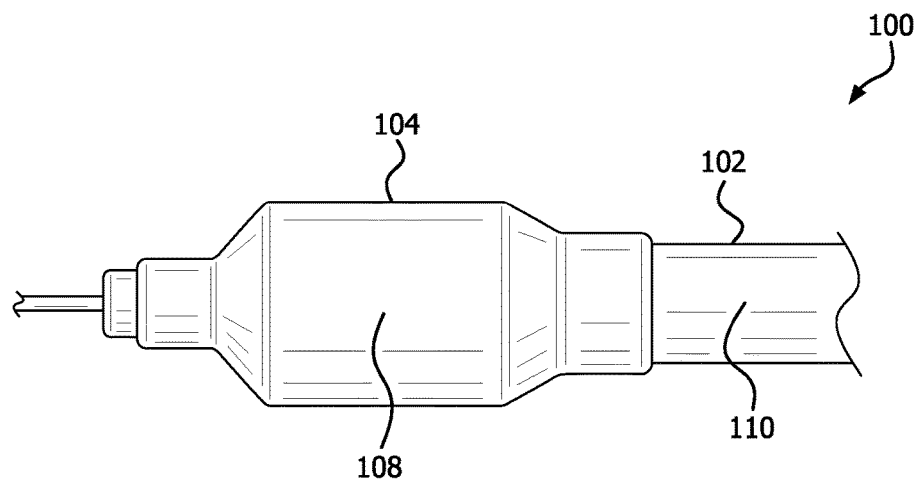
FIGS. 2A and 2B illustrate a balloon inflated to a first pressure from an exterior perspective and in cross section of same, in accordance with various embodiments.
Figure 2B:
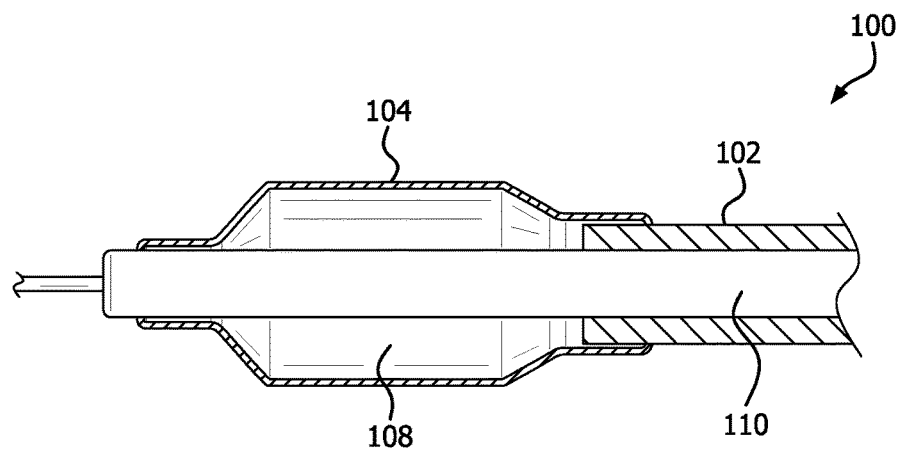

With reference to FIGS. 2A and 2B, inflated balloon assembly 100 is shown. Inflated balloon assembly 100 comprises the same components as labeled and described above with respect to FIGS. 1A and 1B, with balloon 104 in an expanded state due to internal pressure. As shown in FIGS. 2A and 2B, balloon 104 is a balloon having an upper distension limit, i.e., a nominal diameter, size, or dimension, beyond which balloon 104 will not appreciably distend. Thus, at various pressures above a particular value, referred to herein as a first pressure, balloon 104 has a fixed diameter. In various embodiments, the first pressure can be from about 2 atm to about 50 atm. In this manner, a balloon can be inflated to a first pressure to fully expand the balloon and, for example, successfully dilate a vessel.

As described above, in response to a first pressure being reached, the balloon obtains an inflated state. However, in various embodiments, perfusion does not begin at this first pressure. In this regard, perfusion can be regulated in accordance with the internal pressure of the balloon. Stated another way, perfusion can occur at a selectable pressure (i.e., a threshold perfusion pressure) independent from the pressure required for expansion of the balloon. As such, a balloon can be used to deliver therapeutic angioplasty for a short duration, by maintaining the pressure below a threshold perfusion pressure for the short duration, after which a clinician can decide whether or not perfusion is warranted. The clinician could then act to raise the internal pressure of the balloon to a second pressure (e.g., the threshold perfusion pressure or greater) to allow for perfusion. Similarly, a clinician can decide what amount of perfusion is warranted. Alternatively, the balloon could be provided such that the first and second pressures are matched to ensure perfusion during angioplasty, so long as the first pressure is high enough to enable sufficient dilation forces.

In various embodiments, balloons disclosed herein comprise multiple layers, such as a composite material. A layer can comprise one layer of material or a set of layers of material. Layers can be permanently attached, partially attached, or simply disposed adjacent to one another. Various layers can be used to achieve desired balloon characteristic, such as a non-compliant behavior, a certain perfusion rate, a reinforcing layer to withstand internal pressures or provide a desired shape, a layer to contain a therapeutic agent, and the ability for proper wetting of adhesives for attachment of the balloon to an elongate member.

Balloon layers can be disposed within one another, and in various embodiments, bonded using an adhesive or other like material, although in various embodiments no adhesive or like material is used between layers. In various embodiments, balloon layers are sintered together. For example, balloon layers comprised of ePTFE can be disposed coaxially or substantially coaxially within one another in direct contact. Then, the balloon can be brought to a temperature above the melting point of PTFE. The layers can then bond to one another while retaining their respective microstructures.

Figure 3A:
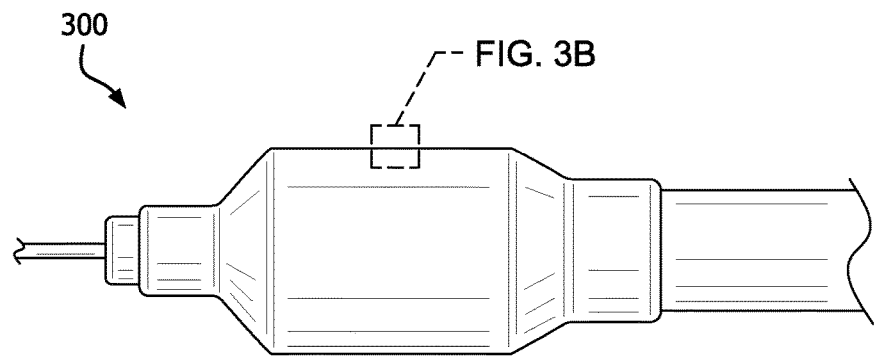
FIGS. 3A and 3B illustrate a balloon comprised of multiple layers, in accordance with various embodiments.
Figure 3B:
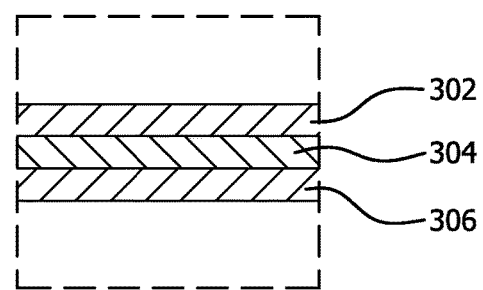

Though any number of balloon layers, including a single layer, is contemplated herein, in various embodiments, two to three layer balloons are used: a weeping control layer, a reinforcing layer, and optionally, a seal layer. In addition, as described herein, a weeping control layer, a reinforcing layer, and seal layer can comprise one or more layers of a given material. For example, with reference to FIGS. 3A and 3B, a three layer balloon 300 is shown. Weeping control layer 306 is shown disposed substantially coaxially with reinforcing layer 304 and seal layer 302. All layers can be comprised of any suitable material, though in various embodiments a fluoropolymer, such as polytetrafluoroethylene ("PTFE") and/or expanded polytetrafluoroethylene ("ePTFE") is used.

In various embodiments, the one or more balloon layers are highly biocompatible. A biocompatible material is hereby defined as a material being suited for and meeting the purpose and requirements of a medical device, used for either long or short term implants or for non-implantable applications. Long term implants are defined as items implanted for more than 30 days.

One or more layers of a balloon can be comprised of PTFE or ePTFE. Alone, or in combination with ePTFE or PTFE, various balloon components can be formed of biocompatible materials, such as polymers which can include fillers such as metals, carbon fibers, glass fibers or ceramics. Such polymers can include olefin polymers, polyethylene, polypropylene, polyvinyl chloride, polytetrafluoroethylene which is not expanded, fluorinated ethylene propylene 45 copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, and natural silk can be included in components of a balloon.

Weeping control layer 306 can comprise a layer which provides the resistance to weeping needed to generate internal pressure. For example, the low surface energy of ePTFE combined with a small pore size yields a suitable material for weeping control layer 306. By providing a membrane with a sufficiently small pore size, sufficient pressure can be generated during inflation before allowing fluid to pass through the layer.

While weeping control layer 306 can be flow resistant to fluid at pressures below the threshold perfusion pressure, weeping control layer 306 may not be flow resistant to air at these lower pressures. In an embodiment, balloon 300 can comprise a porous membrane that is air permeable at a low pressure, e.g. a pressure between about 1 to about 2 atm, and does not perfuse a fluid until pressures equal or exceed 10 atm.

Weeping control layer 306 can be made from ePTFE as described in co-assigned U.S. Pat. No. 7,306,729, entitled, "Porous PTFE materials and articles produced there from," and issued on Dec. 11, 2007, the contents of which are herein incorporated by reference. For example, weeping control layer 306 can comprise a porous PTFE membrane formed by a method comprising forming an extruded lubricated tape of PTFE polymer by a paste extrusion process; stretching the extruded lubricated tape transversely, and drying the stretched tape to remove lubricant; longitudinally expanding the resulting tape; then transversely expanding the tape at an expansion ratio of 20:1. In various embodiments, two to ten layers of ePTFE as described in U.S. Pat. No. 7,306,729 can comprise weeping control layer 306.

Figure 15A:
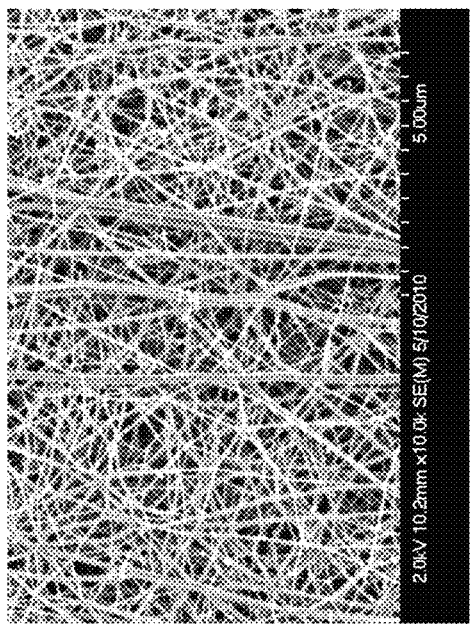
FIGS. 15A to 15C illustrate various porous microstructures of a weeping control layer, wherein the microstructure is substantially fibrillated, in accordance with various embodiments.
Figure 15B:
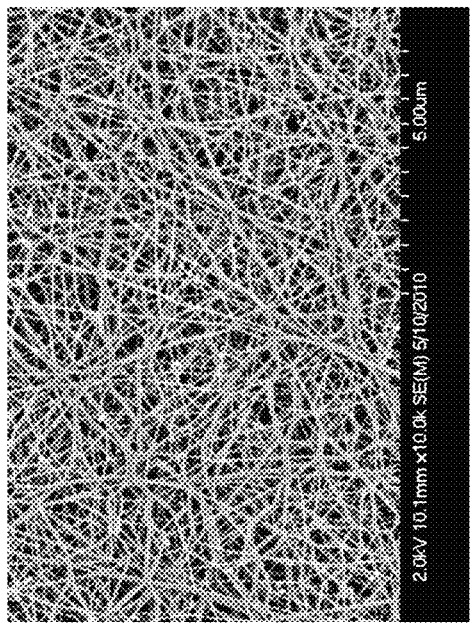
Figure 15C:
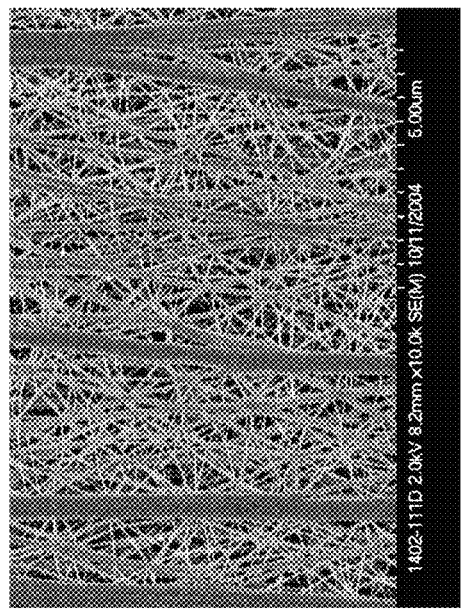

A microstructure of weeping control layer 306 is illustrated in FIG. 15, which depicts a scanning electron micrograph of a sample of ePTFE made generally in accordance with U.S. Pat. No. 7,306,729. FIG. 15 is shown at 1000× magnification.

In various embodiments, weeping control layer 306 comprises a porous membrane characterized by a mean flow pore size, and this mean flow pore size can be only minimally changed before perfusion and during perfusion. Accordingly, balloon 300 with a substantially stable mean flow pore size can allow for multiple inflation and perfusion cycles, e.g., at least two cycles, provided the balloon is not inflated above about 1 atm, about 3 atm, or about 5 atm of the initial perfusion threshold pressure.

In various embodiments, weeping control layer 306, and accordingly balloon 300, can begin to substantially perfuse at a pressure of at least about 2 atm, at least about 6 atm, at least about 12 atm, at least about 15 atm, at least about 20 atm, at least about 25 atm, at least about 30 atm, at least about 40 atm, or at least about 50 atm. In an embodiment, once the threshold perfusion pressure is obtained, weeping control layer, and accordingly the balloon, can perfuse a fluid and/or therapeutic agent at a flux rate of at least about 0.1 cm/min, at least about 0.2 cm/min, at least about 0.5 cm/min, at least about 1 cm/min, at least about 2 cm/min, or at least about 5 cm/min.

Optionally, as previously described, balloon 300 can have a max or terminal pressure. As such, weeping control layer 306 can have a rate of perfusion (ml/s) that is about equal to or greater than the rate of fluid entry (ml/s) into balloon 300, i.e., inflation rate. The terminal pressure can be greater than the pressure at which perfusion begins.

In various embodiments, weeping control layer 306 comprises a porous microstructure, i.e., the weeping control layer 306 has micropores as compared with microbores. As used herein, micropores are typically meandering and are part of the membrane's microstructure; as such, the perfusion path of a fluid through the membrane can comprise a meandering or indirect path through the porous membrane. In comparison, microbores are formed holes that go straight through the layer and can be formed by any known techniques, e.g., laser perforation. In an embodiment, weeping control layer 306 can comprise a substantially fibrillated, porous microstructure.

In accordance with various embodiments, a number of factors can affect performance of weeping control layer 306, e.g., the mean flow pore size, the thickness of weeping control layer 306, presence of nodes or lack thereof, the density of the material, the balance ratios, and the amount of surface area within the weeping control layer's microstructure per unit of mass. These factors can be varied to vary the performance variables of balloon 300. Such performance variables include the perfusion threshold pressures of balloon 300, the terminal pressure value, the ability of the microporous membrane to perform multiple perfusion cycles, and the flux rate. In various embodiments, the film from which the weeping control layer 306 can be constructed can have a microstructure surface area (per gram) of at least about 15 m²/g to at least about 45 m²/g. In various embodiments, the microstructure can be substantially fibrillated; i.e., it comprises very small nodes or is substantially nodeless. By reducing the size of the nodes, fluid flow is less impeded. In various embodiments, the density of the first porous membrane can be less than about 0.3 g/mL. In various embodiments, the film of which the weeping control layer 306 is constructed has a Gurley versus bubble point equal to or below the line defined by the equation log (Gurley)=$5.13 \times 10^{-3}$ (Bubble Point)−1.26. The bubble point can be at least about 100 kPa to at least about 1000 kPa. Test methods to quantify values described herein can be found in U.S. Pat. No. 7,306,729, previously referenced herein.

In various embodiments, balloon 300 can be configured to distend minimally and/or negligibly beyond the nominal diameter. In addition, the nominal diameter can be sufficient to dilate a vessel. Balloon 300 in the expanded state can be capable of dilating any lumen of a body, such as a blood vessel. Similarly, balloon 300 can be expanded to a diameter, size, or dimension that is capable of dilating a stenosis.

Balloon 300 can be any suitable shape, such as generally cylindrical, at least across an intermediate portion. Other shapes can include generally ellipsoidal, spherical, or tapered shapes, or any other shape suitable for a given location or procedure.

Reinforcing layer 304 can provide structural support to a balloon 300 and help to define balloon properties such as shape, diameter, and compliance. Reinforcing layer 304 can tend to provide the ability to withstand the wall stresses of high internal pressures, for example, about 4 atm and as high as about 50 atm, depending on the application and balloon diameter. Thus, materials that have high tensile strength, especially in one direction, (i.e., highly-oriented materials) can be suited for this purpose. Reinforcing layer 304 can be made from ePTFE as described in U.S. Pat. No. 5,476,589, whose contents are herein incorporated by reference. For example, reinforcing layer 304 can comprise a thin porous PTFE membrane consisting essentially of a nonwoven web having a microstructure of substantially only microfibrils fused at crossover points.

Figure 16:
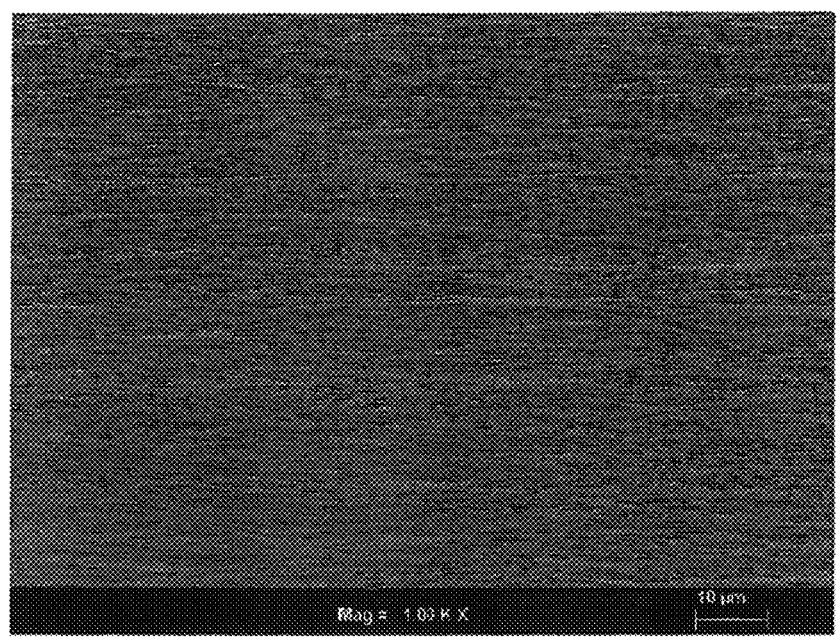
FIG. 16 illustrates the microstructure of a reinforcing layer, in accordance with various embodiments.

With momentary reference to FIG. 16, a microstructure of reinforcing layer 304 is illustrated. FIG. 16 is a scanning electron micrograph of a sample of ePTFE made in accordance with U.S. Pat. No. 5,476,589. FIG. 16 is shown at 1000×.

As noted above, desired rates of perfusion and perfusion threshold pressures can be achieved through appropriate selection of a membrane with the appropriate WEP and/or bubble point, among other factors. Thus, in various embodiments, reinforcing layer 304 can be constructed to perform the functions of weeping control layer 306 through such selection of WEP and/or bubble point. Such embodiments can optionally not include a separate weeping control layer.

Seal layer 302 can provide properties to balloon 300 that better enable it to be bonded to the elongate member. For example, seal layer 302 can improve the adhesive bond between a balloon and elongate member at the distal and proximal ends of the balloon and elongate member. Various forms of ePTFE can be suitable for this purpose. In particular, an ePTFE product with large pores can be suitable for this purpose.

Figure 17:
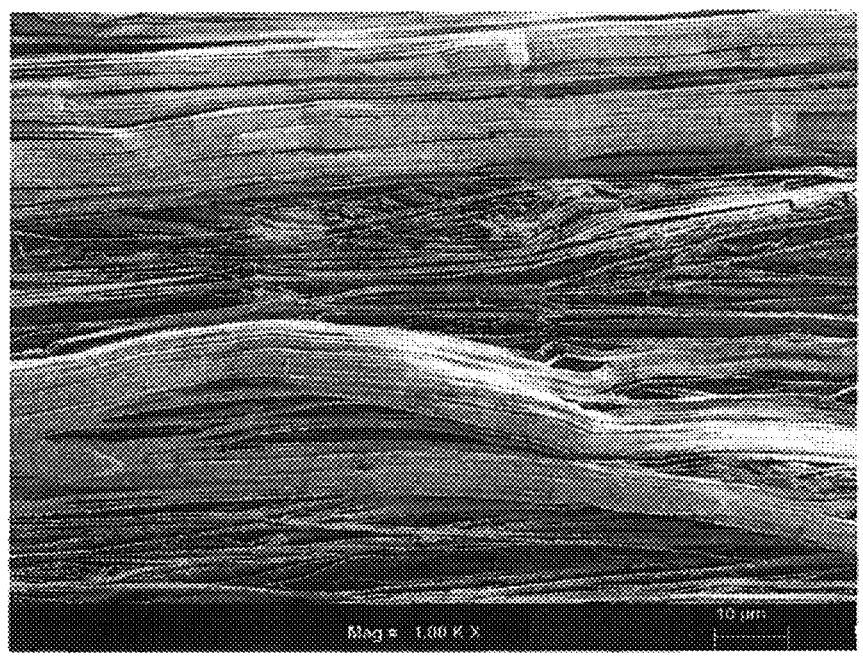
FIG. 17 illustrates the microstructure of a seal layer, in accordance with various embodiments.

With momentary reference to FIG. 17, a microstructure of seal layer 302 is illustrated. FIG. 17 is a scanning electron micrographs of ePTFE with a relatively high degree of openness. FIG. 17 is shown at 1000×.

In various embodiments, layers can be combined where the suitable attributes of both layers can be possessed in a single membrane or layer. For example, reinforcing layer 304 and seal layer 302 can be combined if a membrane with sufficient strength is used that also possesses the suitable openness to allow for proper bonding to the elongate member. Likewise if a membrane is selected which possesses both the suitable characteristics to resist weeping and provide the appropriate mechanical attributes, this membrane could be used to combine weeping control layer 306 and reinforcing layer 304 into a single layer. Or, as another example, if an adhesive is selected which can better penetrate a tight pore, ePTFE structure. Then a distinct sealing layer 302 with a high degree of openness can optionally be omitted.

Figure 4A:
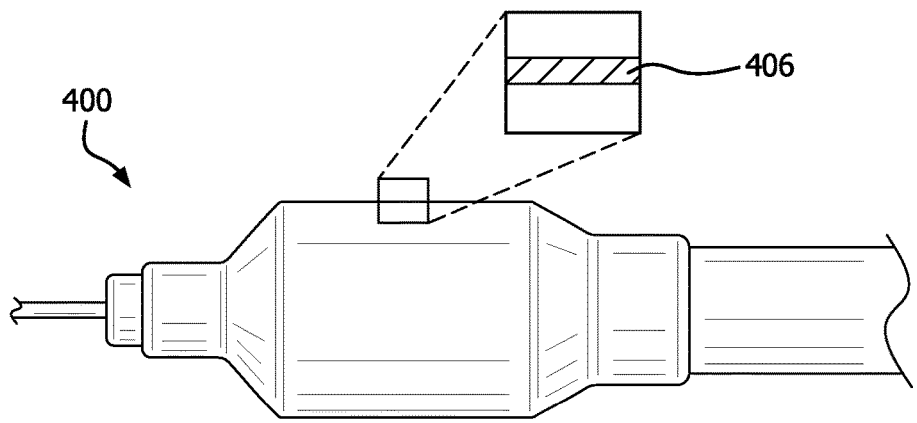
FIG. 4A illustrates a balloon comprised of a first porous membrane, in accordance with various embodiments.
Figure 4B:
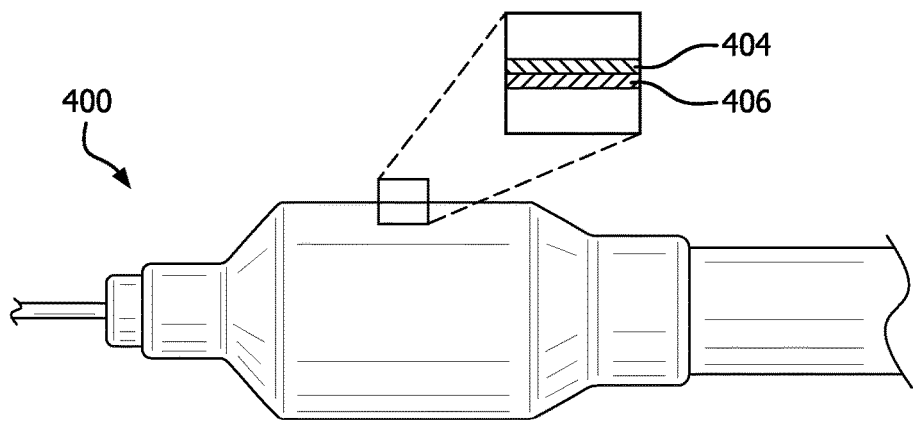
FIG. 4B illustrates a balloon comprised of two porous membranes, in accordance with various embodiments.
Figure 4C:
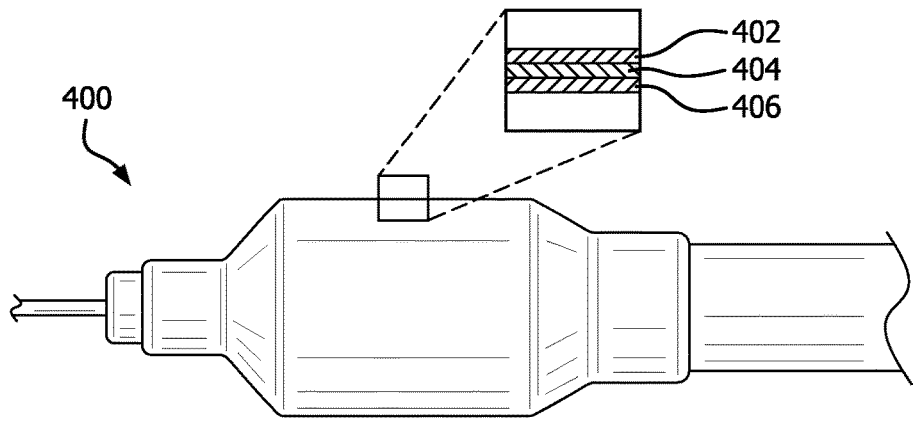
FIG. 4C illustrates a balloon comprised of three porous membranes, in accordance with various embodiments.

In various embodiment, with reference to FIG. 4A to 4C, a balloon 400 can comprise a first porous membrane 406 configured to begin perfusing at a pressure, the pressure being equal to or greater than that required to reach nominal diameter or dimension. Optionally, balloon 400 can further comprise a second porous membrane 404 constructed to withstand the hydrostatic load generated by the first membrane upon inflation. Further still, balloon 400 can comprise a third porous membrane 402 constructed to facilitate sealing balloon 400 to an elongate member, such as a guide wire or an elongate member. The first porous membrane 406 can be the weeping control layer as described herein. The second porous membrane 404 can comprise the reinforcing layer as described herein. Thus, the third porous membrane 402 can comprise the sealing layer as described herein. Optionally, all three porous membranes are configured to perfuse a therapeutic agent. In the case of multiple layers, the layers can maintain contact throughout inflation and perfusion; though in various alternative embodiments, contact between layers is not maintained. In an embodiment, the layers may be sintered together.

Figure 5:
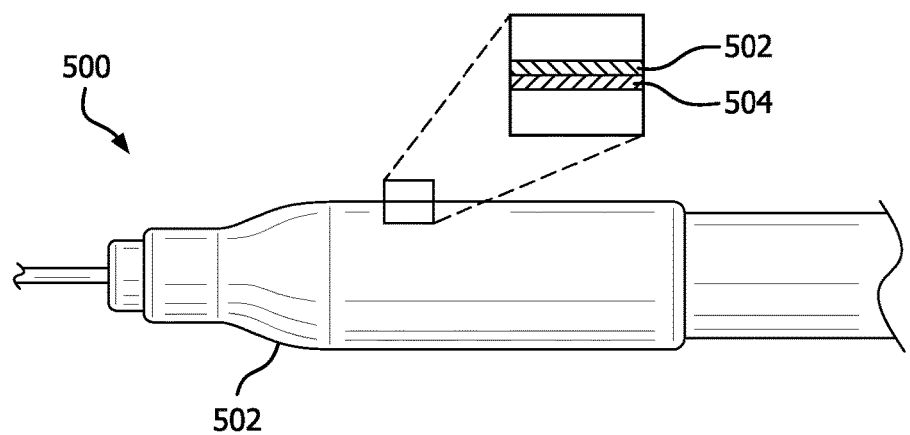
FIG. 5 illustrates a balloon with a therapeutic agent from an exterior perspective, in accordance with various embodiments.

In various embodiments, with reference to FIG. 5, balloon assembly 500 can comprise a controlled perfusion balloon 502 as described herein and a therapeutic agent 504 which can be in the form of dry, liquid, or gel coating placed on an inner and/or outer surface of a layer or membrane. Therapeutic agent 504 can be held within the balloon's interior volume or it can be embedded in or otherwise associated with the walls of a balloon. Therapeutic agent 504 can be adhered to an interior surface of balloon 502 and/or can be sandwiched between two layers in balloon 502 itself. Balloon 502 would then protect the therapeutic agent from dissolution or other release unless and until perfusion began in response to inflation to a second pressure or above. FIG. 5 shows balloon 502 in an uninflated state at a first pressure and thus prior to perfusion. Therapeutic agent 504 is thus retained within balloon 502 until perfusion begins.

Figure 6:
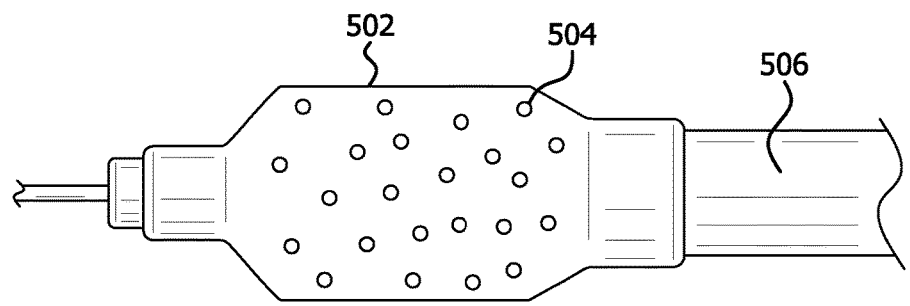
FIG. 6 illustrates a cross-sectional view of an inflated balloon with therapeutic agent, in accordance with various embodiments.

With reference to FIG. 6, shows an expanded balloon 502 with therapeutic agent 504 is shown within the interior volume of balloon 502. Therapeutic agent 504 can be introduced through a lumen of elongate member 506 as part of the inflation fluid. Alternatively, therapeutic agent can be located within interior volume of balloon 502 or elsewhere along the fluid delivery path and be solvated by inflation fluid. Balloon 502 tends to protect the therapeutic agent from release or undesired dilution until perfusion begins in response to inflation to the second pressure. Therapeutic agent 504 is retained within the interior volume of balloon 502 until perfusion begins. In an embodiment, a perfusable balloon assembly can comprise a therapeutic agent 504 coated on the outer diameter portion of elongate member 506 covered by balloon 502.

Similarly, a balloon assembly can comprise a therapeutic agent located along any point within the fluid delivery and inflation pathway. In other embodiments, a balloon can comprise a drug coated on an inner elongate member component (such as a guidewire lumen that extends at least partially into the balloon), coated on the inner diameter of the inflation lumen or hub, or premixed outside the body and injected into the balloon, for example with the inflation media. The location of the therapeutic agent plus its formulation can permit complete dissolution prior to the balloon beginning to weep.

Accordingly, in various embodiments, a balloon device can comprise a porous membrane configured to expand to an expanded state in response to introduction of a fluid at a first pressure, wherein the fluid begins to perfuse through the porous membrane above a second pressure, the second pressure being at least one of equal to and greater than the first pressure, and a therapeutic agent located on section of elongate member underlying the balloon. The porous membrane can begin to substantially perfuse at an internal pressure of at least about 13 atm or more as described herein.

In various embodiments, balloon 502 can comprise a weeping control layer, such as a porous membrane, which is selectively perfusable. The porous membrane can be configured to perfuse a first agent and not perfuse a second agent. The selective perfusion can be controlled by principles of size exclusion, electrostatic repulsion, and/or aromaticity or hydrophobicity interactions. In an embodiment, the second agent can comprise a contrast agent. A selectively perfusable balloon can be beneficial to locate balloon 502 in a precise manner during a perfusion cycle.

Figure 7:
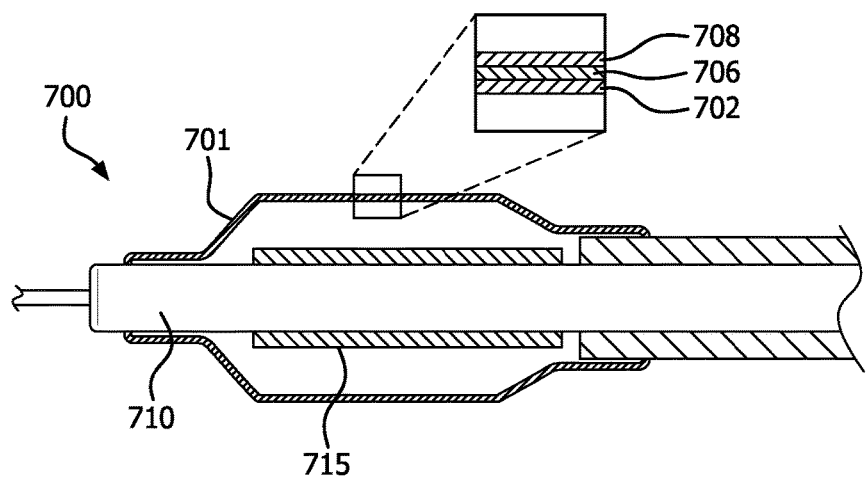
FIG. 7 illustrates an inflated balloon with therapeutic agent in cross section, in accordance with various embodiments.

FIG. 7 illustrates a cross-sectional view of balloon assembly 700. Balloon assembly 700 shows elongate member 710 having a lumen that is in communication with a balloon 701 comprising three layers. Weeping control layer 702 is shown within reinforcing layer 706. Reinforcing layer 706 is illustrated within seal layer 708. Therapeutic agent 715 is a coating on elongate member 710 underlying weeping control layer 702.

In an embodiment, balloon assembly 700 can comprise a porous membrane 702 and therapeutic agent 715, which can be located on section of an elongate member underlying the balloon. Porous membrane 702 can be configured to expand to an expanded state in response to introduction of a fluid at a first pressure, but the fluid does not begin to perfuse through porous membrane 702 until the pressure is at or above a second pressure. The second pressure can be equal to or greater than the first pressure. In an embodiment, the second pressure can be equal to or greater than 13 atm. Stated differently, porous membrane 702 begins to substantially perfuse at a pressure equal to or greater than 13 atm.

In a further embodiment, balloon 701 perfusion can be configured and controlled such that a prescribed dose of therapeutic agent 715 perfuses through balloon 701. In addition, balloon 701 can be configured such that therapeutic agent 715 uniformly perfuses through balloon at least across an intermediate section. Stated differently, therapeutic agent 715 has a perfusion rate at a first area that is substantially equal to a rate of perfusion at an adjacent area.

One key advantage balloon assemblies of the present disclosure offer is that a single device can be used by the clinician to both dilate a lumen or body cavity and either simultaneously or subsequently deliver a therapeutic (or other beneficial) agent. Not having to swap out and use two separate devices (a dilation balloon and perfusion balloon) for these functions saves money and procedure time. The "dilation" referred to here is clinically significant dilation, i.e., dilation produced by relatively high pressures which are required for the desired clinical effect. Such high pressures are required for procedures such as PTA. These are pressures the devices of the present disclosure are capable of withstanding.

Any therapeutic agent that can provide a benefit or previewed benefit to the body is contemplated to be suitable for use with balloons disclosed herein. In particular, therapeutic agents that become safer, more effective, or can achieve another benefit from localized delivery are useful with balloons disclosed herein. Among others, suitable therapeutic agents include antiproliferative, fibrolytic, thrombolytic, antiinflammatory, antiphlogistic, anti hyperplastic, antineoplastic, antimitotic, cytostatic, cytotoxic, antiangiogenic, antirestenotic, microtubule inhibiting, antimigration or antithrombotic therapeutic agents.

For example, suitable therapeutic agents can include: abciximab, acemetacin, acetylvismione B, aclarubicin, ademetionine, adriamycin, aescin, afromoson, akagerine, aldesleukin, amidorone, aminoglutethemide, amsacrine, anakinra, anastrozole, anemonin, anopterine, antimycotics, antithrombotics, apocymarin, argatroban, aristolactam-All, aristolochic acid, arsenic and arsenic-containing oxides, salts, chelates and organic compounds, ascomycin, asparaginase, aspirin, atorvastatin, auranofin, azathioprine, azithromycin, baccatine, bafilomycin, basiliximab, bendamustine, benzocaine, berberine, betulin, betulinic acid, bilobol, biolimus, bisparthenolidine, bleomycin, bombrestatin, boswellic acids and their derivatives, bruceanoles A, B and C, bryophyllin A, busulfan, antithrombin, bivalirudin, cadherins, camptothecin, capecitabine, o-carbamoylphenoxyacetic acid, carboplatin, carmustine, celecoxib, cepharanthin, cerivastatin, CETP inhibitors, chlorambucil, chloroquine phosphate, cictoxin, ciprofloxacin, cisplatin, cladribine, clarithromycin, colchicine, concanamycin, coumadin, C-Type natriuretic peptide (CNP), cudxaisoflavone A, curcumin, cyclophosphamide, cyclosporine A, cytarabine, dacarbazine, daclizumab, dactinomycin, dapson, daunorubicin, diclofenac, 1,11-dimethoxycanthin-6-one, docetaxel, doxorubicin, dunaimycin, epirubicin, epothilone A and B, erythromycine, estramustine, etoposide, everolimus, filgrastim, fluroblastin, fluvastatin, fludarabine, fludarabin-5'-dihydrogenphosphate, fluorouracil, folimycin, fosfestrol, gemcitabine, ghalakinoside, ginkgol, ginkgolic acid, glycoside 1 a, 4-hydroxyoxycyclophosphamide, heparin, idarubicin, ifosfamide, josamycin, lapachol, lomustine, lovastatin, melphalan, midecamycin, mitoxantrone, nimustine, pitavastatin, pravastatin, procarbazin, mitomycin, methotrexate, mercaptopurine, thioguanine, oxaliplatin, bismuth and bismuth compounds or chelates, irinotecan, topotecan, hydroxycarbamide, miltefosine, pentostatine, pegaspargase, exemestane, letrozole, formestane, SMC proliferation inhibitor-2co, mitoxantrone, mycophenolate mofetil, c-myc antisense, b-myc antisense, [3-1apachone, podophyllotoxin, podophyllic acid-2-ethylhydrazide, molgramostim (rhuGM-CSF), peginterferon ct-2b, lanograstim (r-HuG-CSF), macrogol, selectin (cytokin antagonist), cytokin inhibitors, COX-2 inhibitor, NFkB, angiopeptin, monoclonal antibodies which inhibit muscle cell proliferation, bFGF antagonists, probucol, prostaglandins, 1-hydloxyl l-methoxycanthin-6-one, scopolectin, NO donors, pentaerythiltol tetranitrate, syndxloimines, S-nitrosodeilvatives, tamoxifen, staurosporine, [3-oestradiol, ct-oestradiol, oestriol, oestrone, ethinyloestradiol, medroxyprogesterone, oestradiol cypionates, oestradiol benzoates, tranilast, kamebakaurin and other terpenoids, which are used in the treatment of cancer, verapamil, tyrosine kinase inhibitors (tyrphostins), paclitaxel, paclitaxel derivatives, 6-c-hydroxy paclitaxel, 2'-succinylpaclitaxel, 2'-succinylpaclitaxeltile-thanolamine, 2'-glutarylpaclitaxel, 2'-glutarylpaclitaxeltile-thanolamine, T-O-ester of paclitaxel with N-(dimethylaminoethyl) glutamide, T-O-ester of paclitaxel with N-(dimethylaminoethyl)glutamidhydrochloride, taxotere, tissue plasminogen activator (tPA), carbon suboxides (MCS), macrocyclic oligomers of carbon suboxide, mofebutazone, lonazolac, lidocaine, ketoprofen, mefenamic acid, piroxicam, meloxicam, penicillamine, hydroxychloroquine, sodium aurothiomalate, oxaceprol, [3-sitosteiln, myrtecaine, polidocanol, nonivamide, levomenthol, ellipticine, D-24851 (Calbiochem), colcemid, cytochalasinA-E, indanocine, nocadazole, S 100 protein, bacitracin, vitronectin receptor antagonists, azelastine, guanidyl cyclase stimulator tissue inhibitor of metal proteinasel and 2, free nucleic acids, nucleic acids incorporated into virus transmitters, DNA and RNA fragments, plasminogen activator inhibitor-I, plasminogen activator inhibitor-2, antisense oligonucleotides, VEGF inhibitors, IGF-1, active substances from the group of antibiotics such as cefadroxil, cefazolin, cefaclor, cefotixin, tobramycin, gentamycin, penicillins such as dicloxacillin, oxacillin, sulfonamides, metronidazole, enoxoparin, desulphated and N-reacetylated hepailn, tissue plasminogen activator, GpIIb/IIIa platelet membrane receptor, factor Xa inhibitor antibodies, hepailn, hirudin, r-hirudin, PPACK, protamine, prourokinase, streptokinase, warfarin, urokinase, vasodilators such as dipyramidol, trapidil, nitroprussides, PDGF antagonists such as triazolopyilmidine and seramine, ACE inhibitors such as captopril, cilazapill, lisinopill, enalapril, losartan, thioprotease inhibitors, prostacyclin, vapiprost, interferon a, [3 and y, histamine antagonists, serotonin blockers, apoptosis inhibitors, apoptosis regulators such as p65, NF-kB or Bcl-xL antisense oligonucleotides, halofuginone, nifedipine, tocopherol tranilast, molsidomine, tea polyphenols, epicatechin gallate, epigallocatechin gallate, leflunomide, etanercept, sulfasalazine, etoposide, dicloxacillin, tetracycline, triamcinolone, mutamycin, procainimide, retinoic acid, quinidine, disopyramide, flecainide, propafenone, sotolol, naturally and synthetically obtained steroids such as inotodiol, maquiroside A, ghalakinoside, mansonine, strebloside, hydlocortisone, betamethasone, dexamethasone, non-steroidal substances (NSAIDS) such as fenoporfen, ibuprofen, indomethacin, naproxen, phenylbutazone and other antiviral agents such as acyclovir, ganciclovir and zidovudin, clotilmazole, flucytosine, griseofulvin, ketoconazole, miconazole, nystatin, terbinafine, antiprozoal agents such as chloroquine, mefloquine, quinine, furthermore natural terpenoids such as hippocaesculin, barringtogenol C21-angelate, 14-dehydloagrostistachin, agroskeiln, agrostistachin, 17-hydroxyagrostistachin, ovatodiolids, 4,7-oxycycloanisomelic acid, baccharinoids B1, B2, B3 and B7, tubeimoside, bruceantinoside C, yadanziosides N, and P, isodeoxyelephantopin, tomenphantopin A and B, coronailn A, B, C and D, ursolic acid, hyptatic acidA, iso-iildogermanal, cantenfoliol, effusantin A, excisaninA and B, longikauiln B, sculponeatin C, kamebaunin, leukamenin A and B, 13,18-dehydro-6-alpha-senecioyloxychapariln, taxamaiiln A and B, regenilol, triptolide, cymarin, hydroxyanopterin, protoanemonin, chelibu-rin chloride, sinococuline A and B, dihydronitidine, nitidine chloride, 12-beta-hydroxypregnadien-3,20-dion, helenalin, indicine, indicine-N-oxide, lasiocarpine, inotodiol, podophyllotoxin, justicidin A and B, larreatin, malloterin, mallotochromanol, isobutyrylmallotochromanol, maquiroside A, marchantin A, cantansin, lycoridicin, margetine, pancratistatin, liilodenine, bisparthenolidine, oxoushinsunine, periplocoside A, ursolic acid, deoxypsorospermin, psycorubin, ilcin A, sanguinailne, manu wheat acid, methylsorbifolin, sphatheliachromen, stizophyllin, mansonine, strebloside, dihydrousambaraensine, hydroxyusambailne, strychnopentamine, strychnophylline, usambarine, usambarensine, liriodenine, oxoushinsunine, daphnoretin, lariciresinol, methoxylailciresinol, syringaresinol, sirolimus (rapamycin), rapamycin combined with arsenic or with compounds of arsenic or with complexes containing arsenic, somatostatin, tacrolimus, roxithromycin, troleandomycin, simvastatin, rosuvastatin, vinblastine, vincilstine, vindesine, thalidomide, teniposide, vinorelbine, trofosfamide, treosulfan, tremozolomide, thlotepa, tretinoin, spiramycin, umbelliferone, desacetylvismioneA, vismioneA and B, zeoiln, fasudil.

Figure 8:
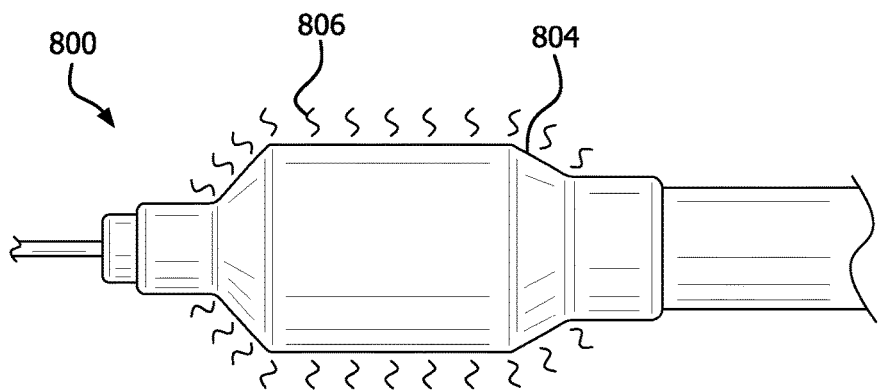
FIG. 8 illustrates an inflated balloon at second pressure in cross section, in accordance with various embodiments.

With reference to FIG. 8, balloon assembly 800 is shown. Balloon assembly 800 is shown at or above a second pressure such that balloon assembly 800 is perfusing. Elongate member 802 is shown having influx fluid 808 under pressure entering the interior volume of balloon 804. Perfusion 806 is shown using exemplary lines, though it is understood that the entire balloon 804 can be made of a permeable material or that only a portion of balloon 804 can be permeable. In various embodiments, a cover, coating or other apparatus can be placed over a portion of balloon 804 to restrict or eliminate perfusion at selected portions of the balloon 804. For example, a cover can be placed over a section of balloon 804 to restrict perfusion from that section. For example, one or both cones of a balloon can be made impermeable by coating these sections or imbibing the porous membrane with a material such as an polymer. Alternatively, apertures or "windows" of various shapes, sizes, and porosity can be present in such covers to provide control over the location of perfusion. In various embodiments, balloon 804 can be constructed of a weeping control layer having a portion that has occluded pores, thus limiting or eliminating perfusion. In this regard, perfusion 806 can be controlled to occur at only a desired portion of balloon 804.

Figure 9:
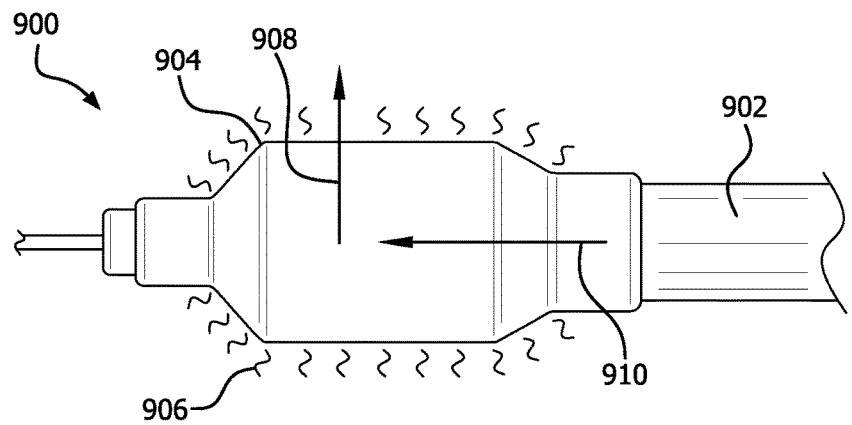
FIG. 9 illustrates an inflated balloon showing perfusion at terminal pressure in cross section, in accordance with various embodiments.

As described above, a terminal pressure can be reached upon the application of pressure to the interior volume of a balloon. Balloon assembly 900 is shown at a terminal pressure in FIG. 9. Thus, the rate of influx of fluid 910 from elongate member 902 into balloon 904 equals or is less than the perfusion rate 908. Perfusion is shown using exemplary lines 906. A terminal pressure can be from about 4 atm to about 60 atm. In this regard, rate of perfusion 908 can be controlled by controlling the rate of influx 910 or the internal pressure of the balloon, but at the terminal pressure, rupture can be prevented.

In various embodiments, balloons disclosed herein can be used to deliver a lytic agent following angioplasty, which can be useful for the opening or removing of thrombus from the lining of blood vessels. In further embodiments, balloons disclosed herein can be used to deliver an anti-proliferative, as described above. In further embodiments, balloons disclosed herein can be used to deliver cold and/or hot fluid (e.g., saline) during percutaneous transluminal angioplasty to control damage to blood vessel or alter the elastic/mechanical properties of the blood vessel.

In various embodiments, a balloon of the present disclosure can be used to deploy a stent within vasculature. A stent can be mounted around the balloon, and the stent can be deployed via inflation of the balloon. The balloon can perfuse a therapeutic agent to provide a therapeutic effect. In some embodiments, a graft material can be configured to take up the therapeutic agent. Therapeutic agent can elute from the graft material for a time after the balloon has ceased perfusion.

In one embodiment, a stent can be affixed to a balloon of the present disclosure using an adhesive that dissolves using a particular solvent. The stent can thus be deployed by inflating a balloon to a first pressure. The adhesive, which can be employed to improve stent retention about the balloon, can be dissolved by increasing the internal pressure of the balloon to a second pressure to cause perfusion of an adhesive dissolving solvent and thereby releasing the stent.

Figure 10:
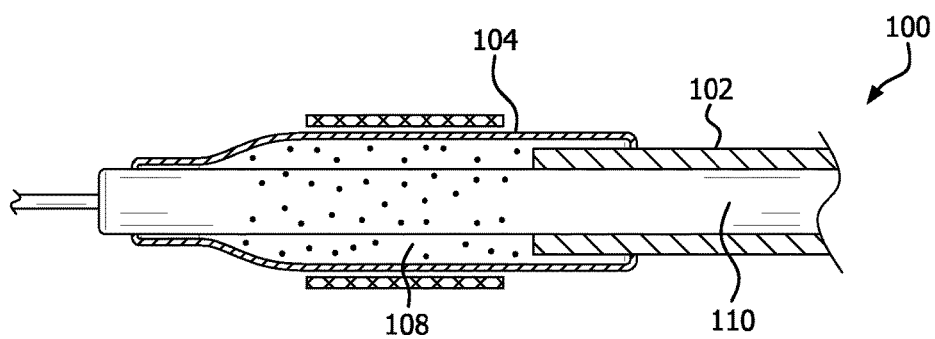
FIG. 10 illustrates a cross-sectional, schematic view of an uninflated balloon with stent from an exterior perspective, in accordance with various embodiments.

For example, with reference to FIG. 10, balloon assembly 100 comprises balloon 106 coupled to elongate member 102. Balloon 106 is disposed within stent 104. Stent 1004 is held in place on balloon 106 using adhesive 108. Adhesive 108 can be any suitable adhesive. Adhesive 108 can be selected to dissolve upon contact with an adhesive dissolving solvent which can be organic or inorganic solvent suitable for use herein. Balloon assembly 100 is positioned within the vasculature at a point where a stent 104 can be beneficial. An adhesive dissolving solvent 110 can be embedded within balloon 106 or can be provided through fluid media through elongate member 102.

Figure 11:
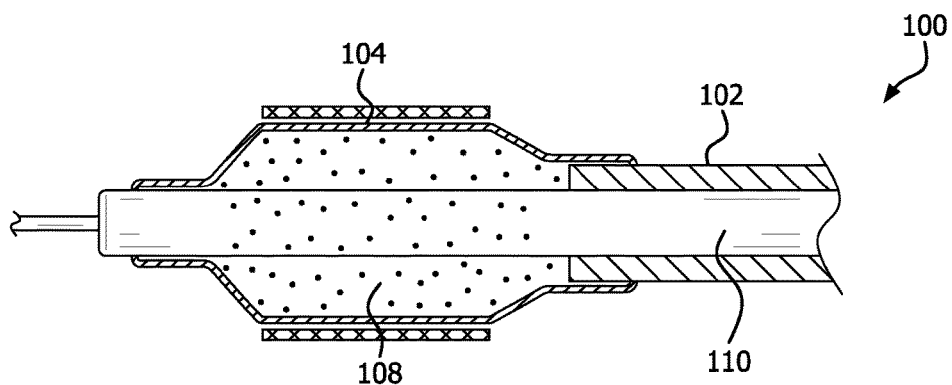
FIG. 11 illustrate a cross-sectional, schematic view of inflated balloon with stent from an exterior perspective and in cross section of same, in accordance with various embodiments.

With reference to FIG. 11, inflated balloon assembly 100 is shown. Inflated balloon assembly 100 illustrates a balloon assembly in an inflated state with stent 104 in a deployed state. Adhesive dissolving solvent 110 is shown dissolving adhesive 108. The dissolution of adhesive 108 allows balloon 106 to become separated from stent 104 and thus be removed from the site of the stent. In an embodiment, a suitable adhesive comprises a hydrophilic agent like polyvinyl alcohol, and the adhesive solvent would comprise an aqueous solution that could hydrate the polyvinyl alcohol and thus cause release of the stent.

Figure 12A:
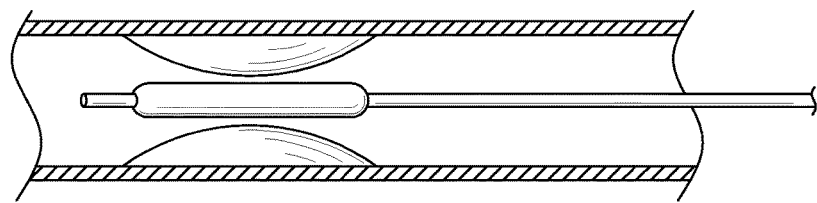
FIG. 12A illustrates a uninflated balloon within vasculature, in accordance with various embodiments.
Figure 12B:
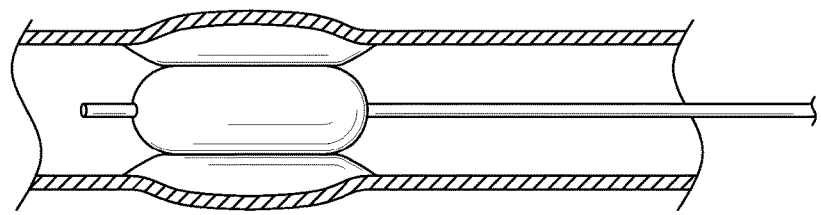
FIG. 12B illustrates an inflated balloon within vasculature at nominal diameter at a first pressure, in accordance with various embodiments.
Figure 12C:
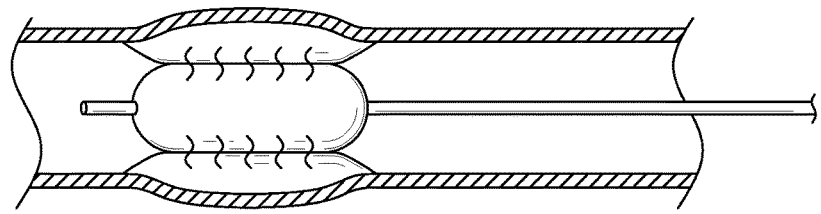
FIG. 12C illustrates an inflated balloon within vasculature at nominal diameter at a second pressure, in accordance with various embodiments.

With reference to FIGS. 12A to 12C, balloon 1200 in vessel 1200 is shown. Catheter 1204 supplies balloon 1200 with fluid to alter the internal pressure of balloon 1200. An uninflated balloon 1200 is shown positioned in vasculature at a treatment site 1220 in FIG. 12A. In FIG. 12B, balloon 1200 is shown in an expanded state at nominal diameter at a first pressure in engagement with blood vessel 1202. In FIG. 12C, balloon 1200 is shown in an expanded state at nominal diameter at a second pressure in engagement with blood vessel 1202 and perfusing therapeutic agent 1208. In an embodiment, balloon 1200 can also be used for anchoring or may be used to resist withdrawal of catheter 1204.

Various embodiments of the herein disclosed balloons can be made in any suitable manner. For example, method 1300 is shown in FIG. 13. Method 1300 comprises step 1302, which comprises fabricating a balloon as described herein In an embodiment, fabricating balloon can comprise tape wrapping a first porous membrane to form the weeping control layer, and further comprise tape wrapping a second porous membrane around at least a portion of the first porous membrane to form the reinforcing layer. Step 1304 comprises disposing the balloon fabricated in step 1302 on an elongate member having a lumen. A balloon can be coupled to the elongate member by, for example, the use of a suitable adhesive. In addition, step 1304 can comprise placing the lumen of the elongate member in fluid communication with the balloon such that fluid can be conducted from the elongate member to the interior volume of the balloon.

In various embodiments, method 1400 can be used. Method 1400 comprises step 1402, which comprises inserting a balloon into a lumen. Any lumen of a mammal or other animal can be used step 1402, for example blood vessels. Step 1404 comprises inflating the balloon to first pressure. Step 1404 can include introducing fluid into the interior volume of a balloon to a first pressure, for example that is useful for dilation, wherein the first pressure is at or below the WEP of the balloon. Step 1404 thus comprises the inflation of a balloon to a fixed diameter with sufficient force to dilate a lumen. Step 1406 comprises inflating the balloon to second pressure. Step 1406 thus comprises introducing fluid into the interior volume of a balloon to a second pressure, wherein the second pressure is at or greater than the first pressure and wherein the first pressure can be the same or above the WEP of the balloon. Perfusion can thus begin in step 1406 and, as described herein, perfusion can be controlled by the selection of pressure or rate of fluid influx applied to the interior volume of the balloon. Fluid can comprise a therapeutic agent, which is delivered to surrounding tissue upon perfusion.

The following examples illustrate making a first porous membrane and a correlation between perfusion through a balloon, as described above, and bubble point values of membranes used in the balloon.

Example 1

Method of Making a Controlled Perfusion Balloons Comprising Three Porous Membranes as Described Herein Four perfusion balloons in accordance with the present disclosure were constructed as follows. Expanded polytetrafluoroethylene (ePTFE) membranes made as generally described in co-assigned U.S. Pat. No. 7,306,729 entitled "POROUS PTFE MATERIALS AND ARTICLES PRODUCED THEREFROM" and described in Example 1 were obtained. The membranes were selected to possess a range of bubble point (BP) values (kPa) yet be of similar mass per unit area (grams per square meter (gsm)). The membranes exhibited the following characteristics: Membrane 1: BP=965 kPa, mass=7.4 gsm; Membrane 2: BP=800 kPa, mass=5.1 gsm; Membrane 3: BP=683 kPa, mass=4.8 gsm; Membrane 4: BP=483 kPa, mass=5.4 gsm. Each membrane was slit to a 0.64 cm width as measured across the transverse direction. These membranes served as the first porous membranes/weeping control layers of the balloons (as described herein).

An ePTFE membrane serving as the reinforcing layer (as described above) was obtained. The membrane was 2.5 cm wide (transverse to the machine direction). The membrane is of a type possessing the following typical characteristics: matrix tensile strength, machine direction: 1227 kPa; density: 0.27 g/cc; mass per area: 2.43 gsm; bubble point: 4.8 kPa.

The same ePTFE membrane used as the reinforcing layer was slit to a 9 mm width (transverse to the machine direction) to create film seals for use in sealing the balloon necks to the catheter as described below.

The perfusion balloons were assembled as follows:

A 6 mm diameter stainless steel mandrel was obtained and coated with a PTFE lubricant. A weeping control layer membrane was helically wrapped around the mandrel at a pitch of 2.5 mm. A second pass of the wrapping was made in the opposite direction to produce helically opposed wraps. A total of about 4 layers were applied.

A reinforcing layer membrane was helically wrapped over the weeping control layer at a pitch of 2.5 mm. A second pass of the wrapping was made in the opposite direction to produce helically opposed wraps. Another two passes were wrapped in a similar manner to produce four passes total upon the mandrel. A total of 40 layers of the membrane were applied.

The wrapped construct was baked in an oven at 380° C. for 11 minutes. The wrapped tube was removed from the mandrel and longitudinally necked until the inner diameter of the tube was below 1.7 mm. The necked tube was then placed on a 1.7 mm stainless steel mandrel and overwrapped with a sacrificial ePTFE membrane wrap. The tube was then axial compressed until it was 70% of its original length to "store length". The construct was then baked in an oven at 380° C. for 1 minute to set the stored length. The sacrificial overwrap was removed and the tube was cut to approximately 70 mm in length to produce the perfusion balloon component.

A dual lumen balloon catheter (PTA 035, Bavarian Medizin Technologies (BMT), Germany) was obtained. The catheter had no balloon at its distal end. The guidewire lumen extended distally past the dual lumen tubing by approximately 60 mm.

The perfusion balloon component was slid onto the dual lumen catheter shaft such that its distal end was approximately 10 mm from the distal end of the catheter. The proximal end of the balloon lay proximal of the open end of the dual lumen (inflation port) by about 20 mm.

Each balloon neck (a 6 mm long section) was compressed into intimate contact with the underlying catheter shaft using a radial compressor at 65° C. A primer (LOCTITE 7701, Henkel Corporation, Düsseldorf, 40589 Germany) was liberally brushed onto the compressed section of balloon at each end of the balloon. Loctite 4981, an adhesive, (Henkel Corporation, Düsseldorf, 40589 Germany) was applied underneath the compressed section of balloon to provide a liquid tight barrier between the balloon and the catheter shaft.

A film seal was applied to balloon neck by radially wrapping 10 layers of a seal layer membrane (as described above) around the compressed section of the balloon. The membrane was continuously imbibed with LOCTITE 4981 as it was wrapped around the compressed section of the balloon. The adhesive was allowed to cure.

Four perfusion balloons were so constructed, each using a different weeping membrane material (Membranes 1-4, as detailed above).

Each of the four balloons was inflated with tap water using a handheld in/deflator. The pressure applied was noted throughout the inflation and the balloon was visually inspected and subjectively characterized for the degree of perfusion. The pressure was noted at which visible perfusion first occurred, where perfusion turned perfuse, and where perfusion occurred at such a high rate that it became difficult to replace the fluid at the rate it was being lost (maximum pressure).

Figure 18:
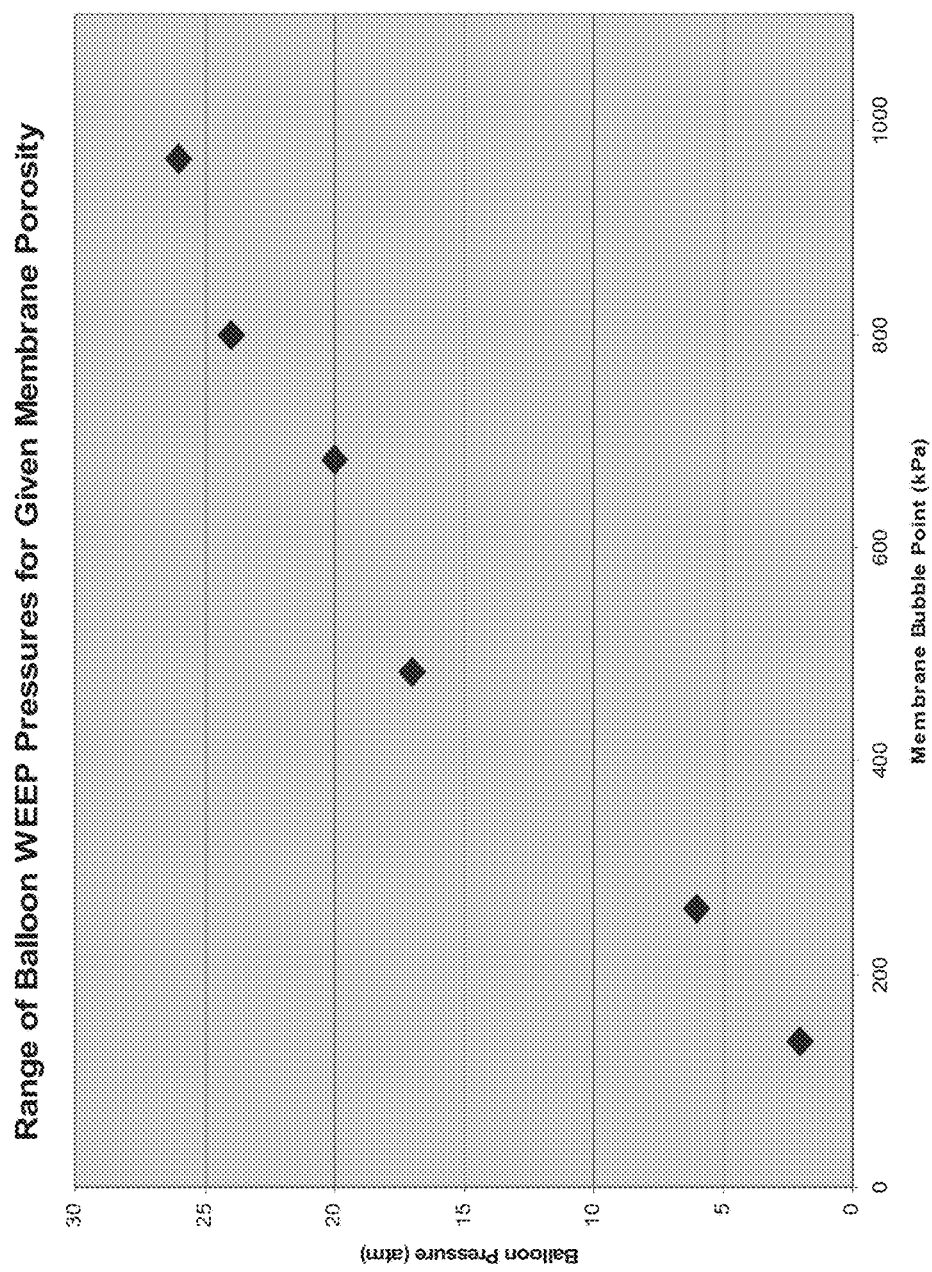
FIG. 18 illustrates a plot of bubble point pressure of a porous membrane against balloon pressure at first weep, i.e., the threshold perfusion pressure.

The results of the testing are shown in FIG. 18. As demonstrated, a very thin lining of a weeping control layer allows the balloon to generate pressures capable of angioplasty. It is also shown that across the range of weeping control layer membranes tested, increasing the bubble point of the membrane will increase the pressure at which the balloon will perfuse and thereby increases the effective pressure with which the balloon can deliver vessel dilation/angioplasty.

Perfusing balloons as described herein can be used in a variety of procedures. For example, in various embodiments, a perfusing balloon as disclosed herein can be used during saphenous vein ablation. A perfusing balloon can be inserted into a vein (e.g., saphenous vein), and inflated with a fluid, such as saline. The blood in the vein can be displaced in response to the inflation of the perfusing balloon. One or more therapeutic agents can then be perfused through the balloon. For example, an anesthetic or other type agent can be perfused by being introduced into the balloon and adjusting balloon pressure accordingly. A therapeutic agent such as a sclerosing agent can then be delivered by being introduced into the balloon and adjusting the pressure applied to the balloon. For example, substantially pure ethanol (i.e., 200 proof) can be delivered as a sclerosing agent in this manner. In another embodiment, the balloon is removed by everting said balloon into a catheter.

In various embodiments, perfusing balloons as described herein can be at least partially coated with polyvinyl alcohol (PVA) to render them more hydrophilic. This could result in the lowering of the perfusion pressure at select sites or across the entire surface.

Similarly, in various embodiments, perfusing balloons as described herein can further comprise an outer layer or coating that is oleophobic or be modified so as to have a low surface energy. For example, as described in U.S. Pat. No. 5,586,279 by Wu, which is hereby incorporated by reference, the reaction product of perfluoroalkyl alkyl alcohol compounds with selected diisocyanates can be applied to the outermost membrane, whether it be the weeping control layer, the reinforcing layer, or the sealing layer, in order to lower the surface energy of the microstructure while preserving the microporous structure. Other examples of oleophobic coatings are described in the following, which are hereby incorporated by reference in their entireties: U.S. Pat. No. 5,342,434 to Wu; U.S. Pat. No. 5,460,872 to Wu and Kaler; WO 2006/127946 to Gore Enterprise Holding; and Canadian Patent No. 2609327 to Freese.

Figure 19A:
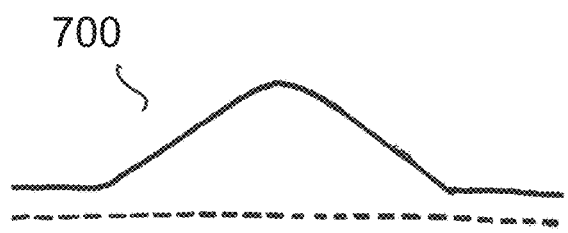
FIG. 19A to 19C illustrates a cross-sectional view of a perfusing balloon that inflates first at a longitudinal center.
Figure 19B:
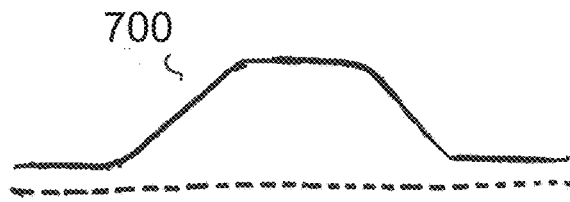
Figure 19C:
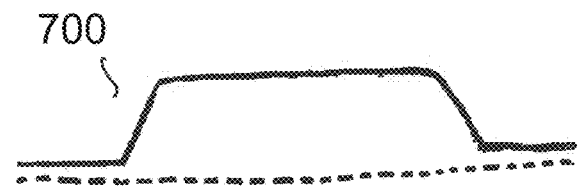
Figure 20A:
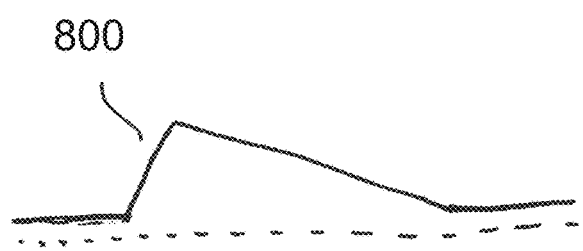
FIG. 20A to 20C illustrates a cross-sectional view of a perfusing balloon that inflates first at a first end and then gradually inflates toward a second end.
Figure 20B:
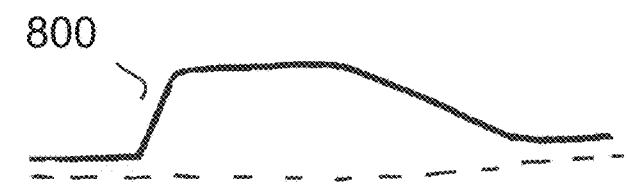
Figure 20C:
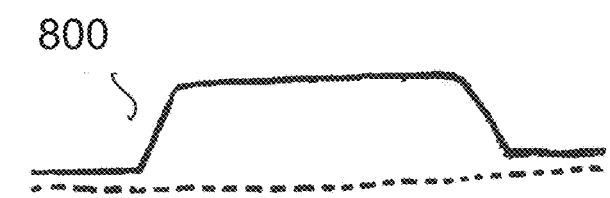

In other embodiments, perfusing balloons as described herein can comprise balloons that have controlled or variable inflation profiles. Such inflation profiles can be, for example, middle-out, where the middle of the balloon increases in diameter first, followed by inflation toward and ultimately including the ends; distal to proximal where the distal end inflates first and inflation progresses proximally; proximal to distal where the proximal end of the balloon inflates first and inflation progresses distally; or ends to middle where both ends of the balloon inflate first and inflation progresses toward the middle of the balloon. For example, with reference to FIG. 19A to 19C, a balloon 1900 that inflates first in its longitudinal center region, and gradually followed by the ends proximal and distal the center region. In other embodiments, with reference to FIG. 20A to 20C, a balloon 2000 can inflate preferentially in either the distal or proximal region, with the opposite region subsequently inflating. Such embodiments, for example, can be useful in tapered lumens, for the controlled delivery of endoprotheses, for ballooning of focal lesions with improved accuracy, or for the control of blood flow during the delivery of a therapeutic agent. In an embodiment, perfusing occurs after the balloon has reached its final diameter along its entirety. In another embodiment, perfusion occurs at a pressure that results in only partial inflation. For example, the balloon may begin to perfuse at a point where the middle of the balloon has inflated, but the ends of the balloon still remain essentially uninflated.

Optionally, in a further embodiment, perfusing balloons as described herein can also comprise tissue disrupting features or pressure concentrators on the outer surface such as needles or wires, such as cutting balloon devices, to improve the therapeutic effect of the perfused agent.

In an embodiment, a balloon having a porous membrane and configured to perfuse a fluid can comprise a textured network on its outer surface. The textured network can be a tissue disrupting feature but does not significantly affect perfusion. For example, in an embodiment, the textured network can be constructed such that the bubble point, Frazier number, and/or gurley of the porous membrane are substantially the same or minimally altered. The textured network can form a coherent irregular network. The network can be formed from thermoplastic elements. U.S. Patent Publication No. 2012/064273 by Bacino entitled "Porous Article" is hereby incorporated by reference in its entirety for purposes of describing a coherent irregular network and various techniques for applying the network to the porous membrane. Some of the details of the Bacino publication are described below.

In an embodiment, the coherent irregular network that may be attached to the porous membrane or made into a free standing article as defined herein is a coherent irregular network of thermoplastic particles attached together. The term coherent as used in defining the coherent irregular network means that the article comprises elements effectively connected together such that the article can be free standing, and therefore does not include discrete particles that may be attached to a substrate, such as fluoroplastic adhesive coated onto a expanded fluoropolymer substrate. The term irregular as used in defining the coherent irregular network means that the structure of the coherent irregular network comprises connecting portions that do not have a consistent diameter or cross-section area across along the length of the connecting portions between intersections or attachments with other connecting portions, particles or elements, and therefore does not included spun-bonded, woven, or felted products that consists of fibers having a consistent cross sectional area. The term network as used in defining the coherent irregular network means that individual elements of the coherent irregular network are effectively attached together to provide a contiguous structure. The coherent irregular network is further defined as comprising porosity between the attached elements throughout the thickness such that the coherent irregular network is porous and permeable. The coherent irregular network is still further defined as having open areas.

A wide range of thermoplastic particles could be used to create the coherent irregular network, including particles having a high molecular weight, or low melt flow index (MFI). Particles with MFI values between 0.2 and 30 g/10 min when tested according to the MFI method described herein may be more desirable. However particles with MFI values greater than 0.1 or less than 50 g/10 min may also be used. In addition, fluoroplastic particles including but not limited to FEP, EFEP, PFA, THV, PVDF, CTFE, and the like, and mixtures thereof are desired in some applications.

In an embodiment, the coherent irregular network is attached to the porous membrane and has a surface roughness defined by a $S_p$ value of at least 35 μm. The size, type, and blend of the particles can be selected to get a desired degree of surface roughness. In addition, using two or more different types of particles can aid in attaching the coherent irregular network to the expanded fluoropolymer layer, attaching the permeable layer to a support layer, or provide a desired permeability, porosity, surface area, abrasion resistance, surface roughness, free standing film strength, or electrical conductivity or the like.

The coherent irregular network disposed on at least a portion of the outer surface of a porous membrane can comprise attached thermoplastic elements that have been fused together creating a network having connecting portions, porosity, and open areas. Open areas as used herein are defined as areas of porosity in the coherent irregular network that extend completely through the thickness of the material. The coherent irregular network does not completely occlude the surface of the underlying porous membrane, and the areas where the porous membrane can be identified through the coherent irregular network are open areas. The "size" of an open area as used herein is defined as being the distance of the longest straight line that can be drawn across the open area. Upon inflation of the balloon, the size of the open area can increase in size as the elements of the textured network become separated. This increase in size can further increase the "grittiness" of the balloon.

In one embodiment, the coherent irregular network further comprises non-melt processible particles. The nonmelt processible particles may be inorganic particle, such as silica, carbon, and the like, or a non-melt processible polymer such as polyimide, PPS, PTFE, or the like. In these embodiments, the thermoplastic particles or elements are attached to create a coherent irregular network, and the non-melt processible particles are attached therein or thereon.

In accordance with the above description, in an embodiment, a balloon can comprise a porous membrane having an outer surface and configured to inflate to a nominal dimension in response to introduction of a fluid at a first pressure, wherein the fluid begins to substantially perfuse through the membrane at a second pressure, the second pressure being at least equal to or greater than the first pressure; and a textured network disposed on at least a portion of the outer surface of the porous membrane and comprising a plurality of voids. The textured network can be a coherent irregular network of thermoplastic elements. In addition, the portion of the outer surface of the porous membrane can comprise an $S_p$ value of at least 35 μm.

Balloons with controlled or variable inflation profiles can be constructed as follows. In one embodiment, a cover may be created by wrapping a film membrane around the balloon. The number of wrapped layers varies along the length of the balloon with fewer layers being positioned over the balloon where expansion is desired to occur first. For example, middle-out inflation is achieved by wrapping a larger number of layers on the distal and proximal ends of the balloon, leaving fewer layers in the middle of the balloon. The stress exerted by the balloon on the cover layers during balloon inflation meets a lower resistance in the middle of the balloon in this case, allowing the middle to expand first. This same concept can be applied to control inflation in the directions distal to proximal, proximal to distal, or ends to middle simply by varying the layers comprising the cover accordingly such that fewer layers are used where preferential inflation is desired.

In various embodiments, a distal cap can be used to secure the distal terminus of a balloon or an elongate member. A distal cap can be referred to as an olive. The olive abuts against the distal end of a balloon or elongate member. An olive can be adhesively bonded to a balloon or elongate member using any of a variety of well-known, biocompatible adhesives which would be readily known and available to those of ordinary skill in the art. Alternatively, olive can be screw threaded, heat bonded, spin welded, or fixed to a balloon or elongate member by a variety of other known techniques which would be equivalent for purposes of this disclosure. Moreover, an elongate member or other apparatus can be disposed on the distal terminus of a balloon. Additionally, the elongate member can provide a lumen through its entirety allowing for the elongate member to be advanced coaxially over a guidewire without leaking of the inflation media.

In various embodiments, balloons disclosed herein can be steerable when in both inflated and/or uninflated states. In further embodiments, balloons disclosed herein can have controllable topographies, meaning their surfaces can be non cylindrical, irregular, feature protrusions or be patterned.

Without intent of limiting, devices disclosed herein (e.g., pressure response perfusing balloons) are useful in any medical applications or treatments such as, for example, angioplasties, cancer therapies, thrombectomies, embolectomies, angioplasty/stenting; angioplasty/stenting in the kidneys; angioplasty/stenting in blood carrying passageways; angioplasty/stenting in the legs; angioplasties of graft-artery anastomotic strictures; cancer of the adrenal cortex; cancer of the endometrium; cancer of the larynx (voice box); cancer of the pancreas; cancer of the parathyroid; cancer of the thyroid gland; cancer of tissues of the lip or mouth (e.g.; tongue; gums; lining of cheeks; bottom of mouth; hard & soft palate; retromolar trigone); cancers; cancers of the blood; cancers of the nasal cavity; candidiasis; capsules; carcinoid syndrome; carcinoid tumors; cardiovascular disease (CVD); cardiovascular patches; carotid artery stenting (CAS); casts; catheters; cells; choriocarcinoma; chronic myeloid leukemia (CML); deep venous thrombosis (DVT); delayed release grafts; delayed release stent-grafts; delayed release stents; dialysis access applications; dialysis equipment; dialysis grafts; drug delivery devices; drug-eluting grafts; drug-eluting implants; drug-eluting sutures; drug-eluting stents; endoprosthesis stent-grafts; endovascular aneurysm repair (EVAR); endografts; endovascular grafting; endovascular stent-grafts; endovascular therapy; esophageal stenting; eustachian tube dysfunction; iliac stents and stent-grafts; immunizations; infection (e.g. in the lungs; throat; sinuses; kidneys; bladder; abdomen; and skin); infections of female reproductive organs; infections of the urinary and lower respiratory tract; infections of throughout the body (septicemia); inflammatory bowel disease (e.g., Crohn's disease); interatrial defects; influenzas; injuries; insomnia; internal thoracis artery grafts (ITA, mammary artery); intestinal stents; intestinal stent-grafts; medical devices; modified release stent-grafts; modified release stents; nephroureteral stenting; neurological devices; pancreatic stenting; pancreatic cancer; pancreas; pancreatitis; percutaneous angioplasty of Takayasu arteritis; penile implants; peripheral vascular stents and stent-grafts; positioning in urethral lumen; pulmonary conditions; radial artery grafts; rectal stents and stent-grafts; reduction or shrinkage of aneurismal (sac); regrow nerve fibers or organs; reinforce collapsing structures; renal cell cancer; renal cell carcinoma (RCC) tumors; renal impairment; renal grafts; renal stents and stent-grafts; renal transplants; renal transplants; repair of aneurysms; repair of living cells; tissues or organs; stenosis of the renal artery (e.g., at ostium); stent-grafts; stenting; stents; stents in femoral arteries; surgical procedures; sustained released grafts; sustained release stent-grafts; thoracic aneurysm repair; thrombosis; thrombotic conditions; treatment of other diseases, cells, tissue, organs, bones, referenced in Gray's Anatomy and disorders (herein incorporated in its entirety as a reference); or combinations thereof, for example.

Benefits, other advantages, and solutions to problems have been described herein with regard to specific embodiments. However, the benefits, advantages, solutions to problems, and any element or combination of elements that can cause any benefit, advantage, or solution to occur or become more pronounced are not to be construed as critical, required, or essential features or elements of any or all the claims of the disclosure. Many changes and modifications within the scope of the instant disclosure can be made without departing from the spirit thereof, and the disclosure includes all such modifications. Corresponding structures, materials, acts, and equivalents of all elements in the claims below are intended to include any structure, material, or acts for performing the functions in combination with other claim elements as specifically claimed. The scope of the disclosure should be determined by the appended claims and their legal equivalents, rather than by the examples given above.

The invention claimed is:

1. A balloon comprising:
a first porous membrane comprising a first microstructure, the first microstructure being configured to inflate to a nominal dimension in response to introduction of a fluid at an inflation pressure and an inflation rate, and resist fluid flow through the first porous membrane at pressures below a threshold perfusion pressure at which perfusion begins; and
a second porous membrane comprising a second microstructure that is different from the first microstructure, the second porous membrane being configured to withstand a hydrostatic load generated by the first membrane upon inflation,
wherein the threshold perfusion pressure is equal to or greater than the inflation pressure required to achieve the nominal dimension, and
wherein a terminal pressure, at which a maximum working pressure of the balloon is exceeded, is greater than the threshold perfusion pressure, and at the terminal pressure, a perfusion rate of the first porous membrane is about equal to or greater than the inflation rate,
wherein the perfusion rate is volume of fluid flowing through pores of the first porous membrane per unit time and the inflation rate is volume of fluid introduced into the first porous membrane per unit time.

2. The balloon of claim 1, wherein at least one of the first porous membrane and the second porous membrane comprise expanded polytetrafluoroethylene (ePTFE).

3. The balloon of claim 1, wherein the first porous membrane comprises a mean flow pore size which is substantially the same before the perfusion and during the perfusion.

4. The balloon of claim 1, wherein the first porous membrane and the second porous membrane are configured to perfuse a therapeutic agent.

5. The balloon of claim 1, wherein the balloon is conformable.

6. The balloon of claim 1, wherein the first porous membrane is disposed at least partially within the second porous membrane.

7. The balloon of claim 1, further comprising a third porous membrane, wherein the second porous membrane is at least partially within the third porous membrane, wherein the third porous membrane facilitates adhesion to an elongate member.

8. The balloon of claim 1, wherein a therapeutic agent is disposed on an outer surface of the first porous membrane.

9. The balloon of claim 1, wherein a size of the balloon in an expanded state is capable of dilating a lumen of a body.

10. The balloon of claim 1, wherein the balloon is air permeable at a pressure less than the threshold perfusion pressure.

11. The balloon of claim 1, further comprising a stent and an adhesive agent, wherein the stent is disposed over at least a portion of the balloon and the adhesive agent adheres the stent to the balloon.

12. The balloon of claim 11, further comprising a solvent, wherein the solvent is capable of perfusing through the first porous membrane and the second porous membrane and dissolving the adhesive agent.

13. The balloon of claim 1, wherein the first porous membrane is configured to perfuse a first agent and not perfuse a second agent.

14. The balloon of claim 13, wherein the second agent comprises a contrast agent.

* * * * *